United States Patent [19]

Hashimoto et al.

[11] 4,234,724
[45] Nov. 18, 1980

[54] CEPHALOSPORIN ANALOGUES AND PROCESSES FOR THE PREPARATION THEREOF

[75] Inventors: Masashi Hashimoto, Takarazuka; Keiji Hemmi, Kyoyo; Matsuhiko Aratani, Osaka; Hidekazu Takeno, Nara; Daijiro Hagiwara, Moriguchi, all of Japan

[73] Assignee: Fujisawa Pharmaceutical Company, Limited, Osaka, Japan

[21] Appl. No.: 972,382

[22] Filed: Dec. 22, 1978

[30] Foreign Application Priority Data

Dec. 23, 1977 [GB] United Kingdom .............. 53735/77
Jun. 16, 1978 [GB] United Kingdom .............. 27116/78

[51] Int. Cl.$^3$ .......................................... C07D 498/04
[52] U.S. Cl. ............................. 544/90; 424/248.51; 424/248.54; 260/239 A
[58] Field of Search ............... 544/90, 92; 424/248.54

[56] References Cited

FOREIGN PATENT DOCUMENTS

| 832174 | 8/1975 | Belgium ................................ 544/90 |
| 848288 | 3/1977 | Belgium ................................ 544/90 |
| 857482 | 2/1978 | Belgium ................................ 544/90 |
| 857621 | 2/1978 | Belgium ................................ 544/90 |
| 2355209 | 11/1973 | Fed. Rep. of Germany ............. 544/90 |
| 2355210 | 11/1973 | Fed. Rep. of Germany ............. 544/90 |
| 52-65292 | 5/1977 | Japan ........................................ 544/90 |

Primary Examiner—John D. Randolph
Attorney, Agent, or Firm—Oblon, Fisher, Spivak, McClelland & Maier

[57] ABSTRACT

Cephalosporin analogues represented by the formula

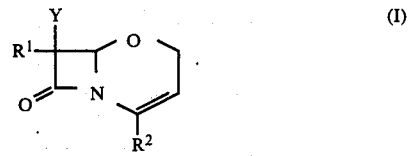

wherein
$R^1$ is amino or a substituted amino,
$R^2$ is carboxy or a protected carboxy, and
$R^3$ is hydrogen or lower alkoxy, processes for making the same, azetidinone intermediates and pharmaceutical compositions comprising said cephalosporin analogues as active ingredients.

23 Claims, No Drawings

CEPHALOSPORIN ANALOGUES AND PROCESSES FOR THE PREPARATION THEREOF

The present invention relates to new cephalosporin analogues and pharmaceutically acceptable salts thereof. More particularly, it relates to new cephalosporin analogues and pharmaceutically acceptable salts thereof which have antimicrobial activities and to processes for the preparation thereof, to pharmaceutical composition comprising the same, and to a method of using the same therapeutically for treatment of infectious diseases in human being and animals.

Accordingly, it is one object of the present invention to provide new cephalosporin analogues and pharmaceutically acceptable salts thereof, which are highly active against a number of pathogenic microorganisms.

Another object of the present invention is to provide processes for the preparation of new cephalosporin analogues and pharmaceutically acceptable salt thereof.

A further object of the present invention is to provide pharmaceutical composition comprising, as active ingredients, said cephalosporin analogues and pharmaceutically acceptable salts thereof.

Still further object of the present invention is to provide a method for treatment of infectious diseases caused by pathogenic bacteria in human being and animals.

The object cephalosporin analogues obtained in Processes 1 to 6 of the present invention can be represented by the following formula (I):

$$R^1\text{—}\underset{\underset{O}{\|}}{C}\text{—}N\diagup\text{O}\diagdown R^2 \quad Y \quad (I)$$

wherein
$R^1$ is amino or a substituted amino,
$R^2$ is carboxy or a protected carboxy, and
Y is hydrogen or lower alkoxy.

The desired object cephalosporin analogues obtained in Processes 4 to 6 and claimed in product claims, which are included within the scope of the object compound (I), are novel and can be represented by the following formula (Ia):

$$R^{1a}\text{—HN}\text{—}\underset{\underset{O}{\|}}{C}\text{—}N\diagup\text{O}\diagdown R^2 \quad Y \quad (Ia)$$

wherein
$R^{1a}$ is acyl selected from the groups consisting of
 ar(lower)alkanoyl which may have a sulfo group, aryloxy(lower)alkanoyl which may have suitable substituent(s),
 lower alkanoyl substituted with an unsaturated 3 to 8-membered heteromonocyclic group containing 1 to 4 nitrogen atom(s) which may have suitable substituent(s),
 lower alkanoyl substituted with an unsaturated 3 to 8-membered heteromonocyclic group containing 1 to 2 sulfur atom(s) and 1 to 3 nitrogen atom(s) which may have suitable substituent(s),
 and a group of the formula: $R^3$—A—CO— in which $R^3$ is aryl or a heterocyclic group which may have suitable substituent(s) and A is carbonyl, hydroxyimino(lower)alkylene, lower alkoxyimino(lower)alkylene, lower alkenyloxyimino(lower)alkylene, lower alkynyloxyimino(lower)alkylene, cyclo(lower)alkoxyimino(lower)alkylene or ar(lower)alkoxyimino(lower)alkylene;
$R^2$ is carboxy or a protected carboxy: and
Y is hydrogen or lower alkoxy.

As to the object compounds (I) and (Ia) and the related compound (e.g. other object compounds, starting compounds, etc.), of the present invention, it is to be understood that there may be one or more stereoisomeric pair(s) such as optical and/or geometrical isomers due to asymmetric asymmetric carbon atom(s) and/or double bond(s) in that molecule, and these isomers are also included within the scope of the present invention. The particulars of such isomers will be made more clear in the following explanation.

Particularly, as to the object compounds of the present invention, it is to be noted that they have, for example, two isomers at the 6th position of the ring, one of which is a so-called oxadethiacephalosporin compound and the basic chemical structure thereof is represented by the following formula, to which there is given a nomenclature, "1-oxadethia-3-cephem", as follows "1-oxadethia-3-cephem"

(Note: In the formula, the mark "◂" means β-configuration and the dotted line means α-configuration.)

Accordingly, it is to be understood that, in all of the under-mentioned explanation of the present invention, the wording "1-oxadethia-3-cephem" means the chemical structure of the formula as shown above.

The cephalosporin analogues (I) and (Ia) of the present invention can be prepared by the following processes.

Process 1

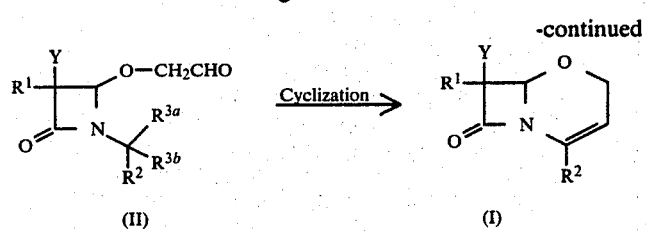

(II)

or its reactive derivatives at the formyl group or a salt thereof

Process 2

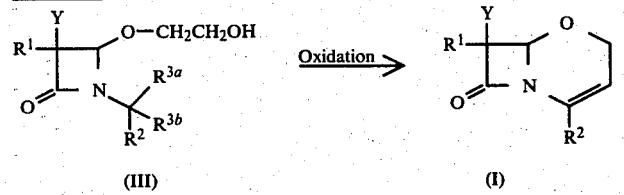

(III)

or its reactive derivatives at the hydroxymethyl group or a salt thereof

Process 3

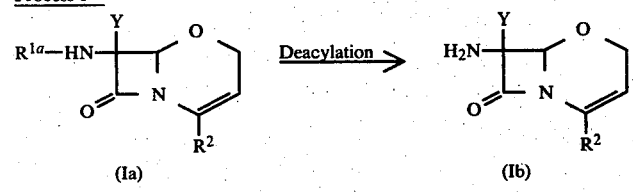

(Ia)

or a salt thereof

Process 4

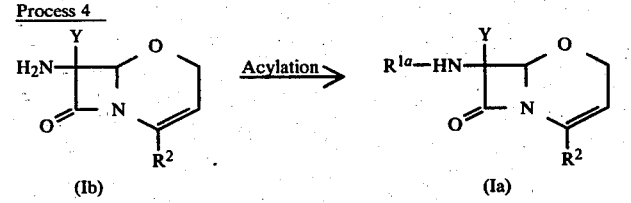

(Ib)

or its reactive derivatives at the amino group or a salt thereof

Process 5

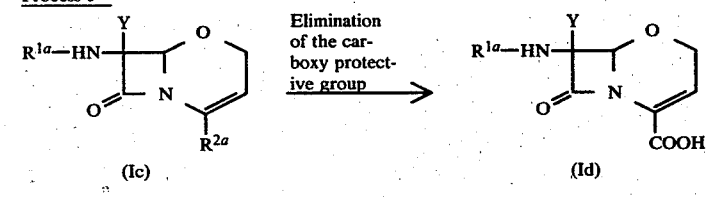

(Ic)

or a salt thereof

Process 6

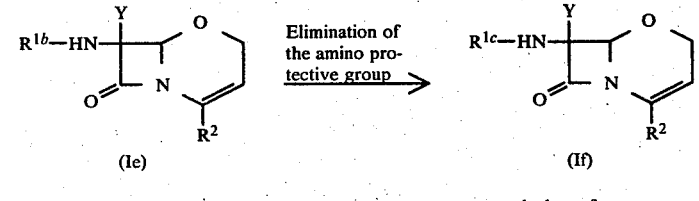

(Ie)

or a salt thereof wherein
$R^1$, $R^{1a}$, $R^2$ and Y are each as defined above;
$R^{1b}$ is lower alkanoyl substituted with an unsaturated 3 to 8-membered heteromonocyclic group containing 1 to 2 sulfur atom(s) and 1 to 3 nitrogen atom(s) which have a protected amino group or a group of the formula:

$R^{3'}$—A—CO— in which A is as defined above and $R^{3'}$ is a heterocyclic group having a protected amino group;

$R^{1c}$ is lower alkanoyl substituted with an unsaturated 3 to 8-membered heteromonocyclic group containing 1 to 2 sulfur atom(s) and 1 to 3 nitrogen atom(s) which have an amino group or a group of the formula:

$$R^{3''}-A-CO-$$

in which A is as defined above and $R^{3''}$ is a heterocyclic group having an amino group;

$R^{2a}$ is a protected carboxy; and $R^{3a}$ is hydrogen and $R^{3b}$ is a group of the formula:

$$-\overset{\overset{O}{\|}}{P}(OR^4)_2$$

in which $R^4$ is lower alkyl, or $R^{3a}$ and $R^{3b}$ are linked together to form a group of the formula:

$$=P(R^5)_3$$

in which $R^5$ is lower alkyl, aryl or di(lower)alkylamino.

The starting compounds (II) and (III) are novel and can be prepared by the processes as illustrated by the following scheme.

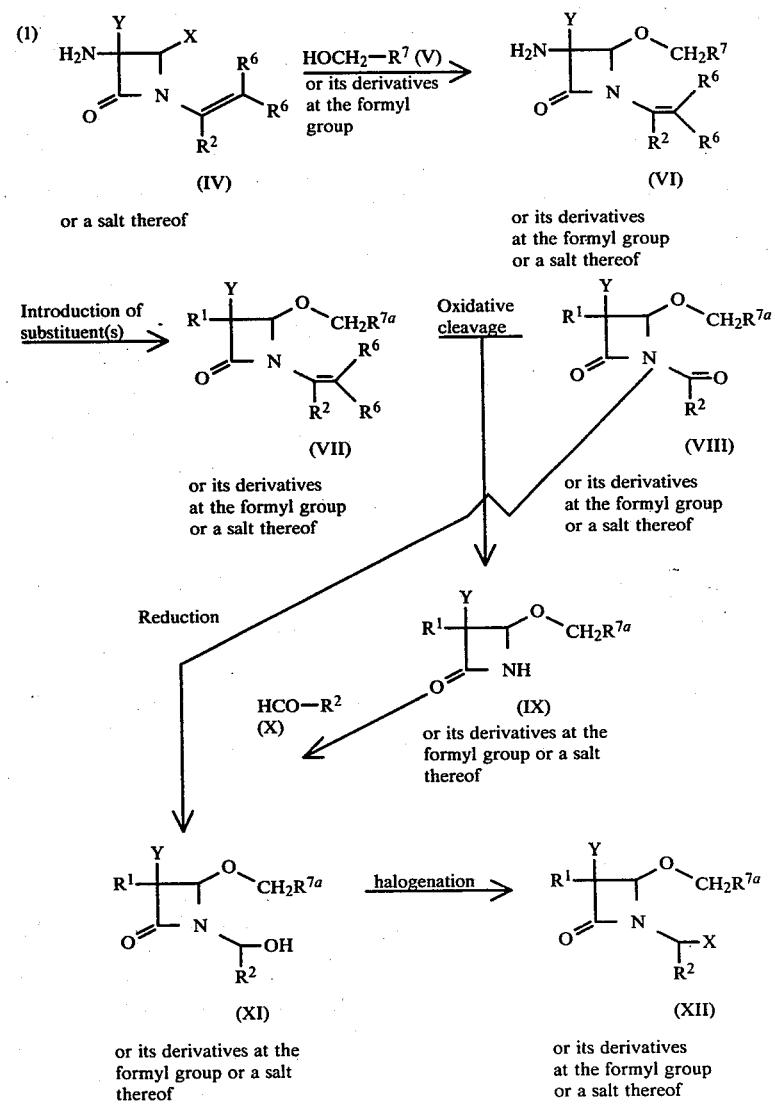

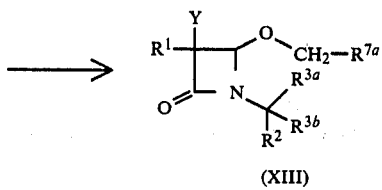

(XIII)

or its derivatives at the formyl group or a salt thereof (2) 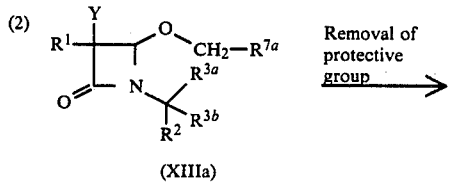 Removal of protective group 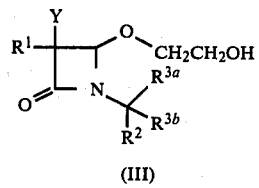

(XIIIa)  (III)

or a salt thereof  or a salt thereof

Oxidation 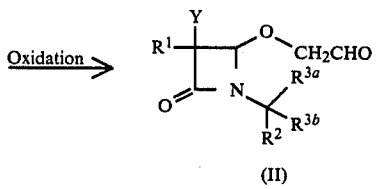

(II)

or a salt thereof wherein $R^1$, $R^2$, $R^{3a}$, $R^{3b}$ and Y are each as defined above;

$R^6$ is lower alkyl;

$R^7$ is hydroxymethyl, a protected hydroxymethyl or formyl;

$R^{7a}$ is a protected hydroxymethyl or formyl;

$R^{7b}$ is a protected hydroxymethyl; and

X is halogen

The starting compound (IV) can be prepared, for example, by the similar manners to those described in Canadian Journal of Chemistry, Vol. 50, pages 2894–2905 (1972).

Suitable pharmaceutically acceptable salts of the object cephalosporin analogues (I) are conventional non-toxic salts and may include a metal salt such as an alkali metal salt (e.g. sodium salt, potassium salt, etc.) and an alkaline earth metal salt (e.g. calcium salt, magnesium salt, etc.), ammonium salt, an organic amine salt (e.g. trimethylamine salt, triethylamine salt, pyridine salt, picoline salt, dicyclohexylamine salt, N,N'-dibenzylethylenediamine salt, etc.), an organic acid salt (e.g. maleate, tartrate, methanesulfonate, benzenesulfonate, toluenesulfonate, etc.), an inorganic acid salt (e.g. hydrochloride, hydrobromide, sulfate, phosphate, etc.), or a salt with an amino acid (e.g. arginine, aspartic acid, lysine, glutamic acid, etc.), and the like.

In the above and subsequent description of the present specification, suitable examples and illustrations for the various definitions to be included within the scope thereof are explained in details as follows.

The term "lower" is intended to mean 1 to 6 carbon atom(s) and "higher" is intended to mean 7 to 18 carbon atoms respectively, unless otherwise provided.

Substituted amino may include an amino group substituted with suitable substituent(s) which is conventionally used in cephalosporin and penicillin chemistry as the substituent of amino group at their 7th or 6th position.

Suitable "substituted amino" may include acylamino, hydrazino, and an amino group substituted with other groups than the acyl groups such as ar(lower)alkyl (e.g. benzyl, phenethyl, trityl, etc.), ar(lower)alkylidene (e.g. benzylidene, 3,5-di(tert-butyl)-4-hydroxybenzylidene, or the like.

Suitable "protected carboxy" may include esterified carboxy in which said ester may be the ones such as lower alkyl ester (e.g. methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g. vinyl ester, allyl ester, etc.);

lower alkynyl ester (e.g. ethynyl ester, propynyl ester, etc.);

mono(or di or tri)-halo(lower)alkyl ester (e.g. 2-iodoethyl ester, 2,2,2-trichloroethyl ester, etc.);

lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. 2-mesylethyl ester etc.); ar(lower)alkyl ester, for example, phenyl(lower)alkyl ester which may have one or more suitable substituent(s) (e.g. benzyl ester, 4-methoxybenzyl ester, 4-nitrobenzyl ester, phenethyl ester, diphenylmethyl ester, bis(methoxyphenyl)-methyl ester, 3,4-dimethoxybenzyl ester, 4-hydroxy-3,5-ditertiarybutylbenzyl ester, etc.);

aryl ester which may have one or more suitable substituent(s) (e.g. phenyl ester, tolyl ester, tertiarybutylphenyl ester, xylyl ester, mesityl ester, cumenyl ester, etc.), and the like.

Suitable "lower alkoxy" may include one which may be branched, for example, methoxy, ethoxy, propoxy, isopropoxy, butoxy, isobutoxy, tert-butoxy, pentyloxy, hexyloxy or the like.

Suitable "lower alkyl" may include one which may be branched, for example, methyl, ethyl, propyl, isopropyl, butyl, isobutyl, t-butyl, pentyl, hexyl and the like.

Suitable "aryl" may include phenyl, tolyl, xylyl, mesityl, cumenyl, naphthyl and the like.

Suitable "di(lower)alkylamino" may include dimethylamino, diethylamino, dipropylamino, methylethylamino and the like.

Suitable "protected hydroxy" moiety in the term "protected hydroxymethyl" may include acyloxy and hydroxy group substituted with other conventional protective group than the acyl groups such as ar(lower)alkyl as aforementioned or the like.

Suitable "halogen" may include chlorine, bromine, fluorine and iodine.

Suitable "acyl moiety" in the terms "acylamino" and "acyloxy" as mentioned above may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, stearoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.); or the like;

Aromatic acyl such as aroyl (e.g. benzoyl, toluoyl, naphthoyl, etc.);

ar(lower)alkanoyl (e.g. phenylacetyl, phenylpropionyl, etc.);

aryloxycarbonyl (e.g. phenoxycarbonyl, naphthyloxycarbonyl, etc.);

aryloxy(lower)alkanoyl (e.g. phenoxyacetyl, phenoxypropionyl, etc.);

arylglyoxyloyl (e.g. phenylglyoxyloyl, naphthylglyoxyloyl, etc.);

arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.);

heterocyclic(lower)alkanoyl (e.g. thienylacetyl, thiazolylacetyl, tetrazolylacetyl, etc.);

heterocyclicglyoxyloyl (e.g. thiazolylglyoxyloyl, thienylglyoxyloyl, etc.); or the like;

in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered more preferably 5 or 6-membered heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

As to the heterocyclic group as mentioned above, the following points are to be noted. That is, in case that the heterocyclic group is specifically thiazolyl group having amino or protected amino as a substituent in its molecule, said thiazolyl group include tautomeric isomers, which are caused by the specific behavior of the thiazole ring. That is, for example, said amino- or protected aminothiazolyl group is represented by the formula:

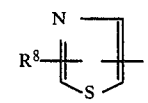

(A)

(wherein $R^8$ is amino or protected amino), and in case that the group of the formula (A) takes the formula:

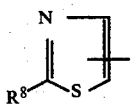

(wherein R⁸ is amino or protected amino), said group of the formula (A′) can also be alternatively represented by its tautomeric formula:

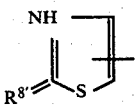

(wherein R⁸′ is imino or protected imino). That is, both of the said groups of the formulae (A′) and (A″) are in the state of tautomeric equilibrium which can be represented by the following equilibrium:

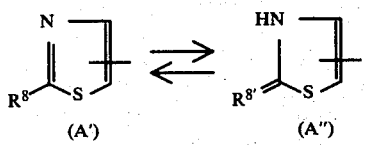

(wherein R⁸ and R⁸′ are each as defined above).

These types of tautomerism between 2-aminothiazole compounds and 2-iminothiazoline compounds as stated above have been well known in the arts, and it is obvious to a person skilled in arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, the object and starting compounds including the group of such tautomeric isomers are represented by using one of the expressions therefor, i.e. 2-amino(or protected amino)thiazolyl and the formula:

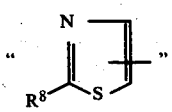

only for the convenient sake. The acyl moiety as stated above may have one to ten, same or different, suitable substituent(s) such as lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower-)alkyl (e.g. cyclopentyl, cyclohexyl, etc.); cyclo(lower-)alkenyl (e.g. cyclohexenyl, cyclohexadienyl, etc.); halogen; amino; protected amino; hydroxy; protected hydroxy; cyano; nitro; carboxy; protected carboxy; sulfo; sulfamoyl; imino; oxo; amino(lower)alkyl (e.g. aminomethyl, aminoethyl, etc.); carbamoyloxy; protected carbamoyloxy; a group of the formula: =N—OR⁹ wherein R⁹ is hydrogen, lower alkyl, lower alkenyl (e.g. vinyl, allyl, 2-butenyl, etc.), lower alkynyl (e.g. ethynyl, 2-propynyl, etc.), cyclo(lower)alkyl (e.g. cyclopropyl, cyclohexyl, etc.) or ar(lower)alkyl such as phenyl(lower)alkyl (e.g. benzyl, phenethyl, etc.).

In this connection, when the acyl moiety has a group of the formula: =N—OR⁹, wherein R⁹ is as defined above, as substituent(s), there are geometrical isomers (syn and anti isomers) due to the presence of double bond. And, for example, the syn isomer means one geometrical isomer having the group of the formula:

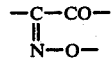

and the corresponding anti isomer means the other geometrical isomer having the group of the formula:

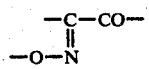

Suitable "ar(lower)alkanoyl which may have a sulfo group" may include phenyl(lower)alkanoyl (e.g. phenylacetyl, phenylpropionyl, etc.), lower alkanoyl substituted with a sulfo and a phenyl groups (e.g. 2-sulfo-2-phenylacetyl, etc.), and the like.

Suitable "aryloxy(lower)alkanoyl in the term aryloxy(lower)alkanoyl which may have suitable substituent(s)" may include phenoxy(lower)alkanoyl (e.g. phenoxyacetyl, phenoxypropionyl, etc.) and the like.

Suitable "unsaturated 3 to 8-membered heteromonocyclic group containing 1 to 4 nitrogen atom(s)" in the term "lower alkanoyl substituted with an unsaturated 3 to 8-membered heteromonocyclic group containing 1 to 4 nitrogen atom(s) which may have suitable substituent(s)" may include the ones as aforementioned.

Suitable "unsaturated 3 to 8-membered heteromonocyclic group containing 1 to 2 sulfur atom(s) and 1 to 3 nitrogen atom(s)" in the terms "lower alkanoyl substituted with an unsaturated 3 to 8-membered heteromonocyclic group containing 1 to 2 sulfur atom(s) and 1 to 3 nitrogen atom(s) which may have suitable substituent(s)", "lower alkanoyl substituted with an unsaturated 3 to 8-membered heteromonocyclic group containing 1 to 2 sulfur atom(s), and 1 to 3 nitrogen atom(s) which have a protected amino group" and "lower alkanoyl substituted with an unsaturated 3 to 8-membered heteromonocyclic group containing 1 to 2 sulfur atom(s) and 1 to 3 nitrogen atom(s) which have an amino group" may include the ones as aforementioned.

Suitable "heterocyclic groups" in the terms "a heterocyclic group which may have suitable substituent(s)", "a heterocyclic group having a protected amino group" and "a heterocyclic group having an amino group" may include the ones as aforementioned as "heterocyclic moiety".

Suitable "lower alkanoyl moieties" in the terms "lower alkanoyl substituted with an unsaturated 3 to 8-membered heteromonocyclic group containing 1 to 4 nitrogen atoms which may have suitable substituent(s)", "lower alkanoyl substituted with an unsaturated 3 to 8-membered heteromonocyclic group containing 1 to 2 sulfur atom(s) and 1 to 3 nitrogen atom(s) which may have suitable substituent(s)", "lower alkanoyl substituted with an unsaturated 3 to 8-membered heteromonocyclic group containing 1 to 2 sulfur atom(s) and 1 to 3 nitrogen atom(s) which have a protected amino group" and "lower alkanoyl substituted with an unsaturated 3 to 8-membered heteromonocyclic group containing 1 to 2 sulfur atom(s) and 1 to 3 nitrogen atom(s) which have an amino group" may include acetyl, propionyl, butyryl, and the like.

Suitable "substituents" in the terms "aryloxy(lower)alkanoyl which may have suitable substituent(s)", "lower alkanoyl substituted with an unsaturated 3 to 8-membered heteromonocyclic group containing 1 to 2 sulfur atom(s) and 1 to 3 nitrogen atom(s) which may have suitable substituent(s)", "lower alkanoyl substituted with an unsaturated 3 to 8-membered heteromonocyclic group containing 1 to 4 nitrogen atom(s) which may have suitable substituent(s)" and "a heterocyclic group which may have suitable substituent(s)" may include lower alkyl (e.g. methyl, ethyl, etc.), lower alkoxy (e.g. methoxy, ethoxy, propoxy, etc.), lower alkylthio (e.g. methylthio, ethylthio, etc.), lower alkylamino (e.g. methylamino, etc.); cyclo(lower)alkyl (e.g. cyclopentyl, cyclohexyl, etc.), cyclo(lower)alkenyl (e.g. cyclohexenyl, cyclohexadienyl, etc.), halogen, amino, protected amino, hydroxy, cyano; nitro, carboxy, protected carboxy, sulfo, sulfamoyl, imino, oxo, amino(lower)alkyl (e.g. aminomethyl, aminoethyl, etc.), and the like.

Suitable "lower alkylene moieties" in the terms "hydroxyimino(lower)alkylene", "lower alkoxyimino(lower)alkylene", "lower alkenyloxyimino(lower)alkylene", "lower alkynyloxyimino(lower)alkylene", cyclo(lower)alkoxyimino(lower)alkylene" and "ar(lower)alkoxyimino(lower)alkylene" may include methylene, ethylene trimethylene, propylene and the like.

Suitable "lower alkoxy moiety" in the term "lower alkoxyimino(lower)alkylene" may include methoxy, ethoxy, propoxy, isopropoxy, butoxy, pentyloxy, hexyloxy and the like.

Suitable "lower alkenyloxy moiety" in the term "lower alkenyloxyimino(lower)alkylene" may include vinyloxy, allyloxy, butenyloxy and the like.

Suitable "lower alkynyloxy moiety" in the term "lower alkynyloxyimino(lower)alkylene" may include ethynyloxy, propynyloxy, butynyloxy and the like.

Suitable "cyclo(lower)alkoxy moiety" in the term "cyclo(lower)alkoxyimino(lower)alkylene" may include cyclopentyloxy, cyclohexyloxy and the like.

Suitable "ar(lower)alkoxy moiety" in the term "ar(lower)alkoxyimino(lower)alkylene" may include phenyl(lower)alkoxy (e.g. benzyloxy, phenethyloxy, etc.) and the like.

Suitable "protected amino group" in the terms "lower alkanoyl substituted with an unsaturated 3 to 8-membered heteromonocyclic group containing 1 to 2 sulfur atom(s) and 1 to 3 nitrogen atom(s) which have a protected amino group" and "a heterocyclic group having a protected amino group" may include acyl as aforementioned and amino group substituted with other conventional protective group than the acyl groups such as ar(lower)alkyl as aforementioned, and the like.

Preferable examples of acyl for $R^{1a}$ are
ar(lower)alkanoyl having a sulfo group, more preferably lower alkanoyl substituted with a sulfo and a phenyl groups (e.g. 2-sulfo-2-phenylacetyl, etc.);
aryloxy(lower)alkanoyl, more preferably phenoxy(lower)alkanoyl (e.g. phenoxyacetyl, phenoxypropionyl, etc.);
tetrazolyl(lower)alkanoyl [e.g. 2-(1H-tetrazol-1-yl)acetyl-3-(1H-tetrazol-1-yl)propionyl, etc.];
aminothiazolyl(lower)alkanoyl [e.g. 2-(2-aminothiazol-4-yl)acetyl, etc.];
protected aminothiazolyl(lower)alkanoyl, preferably acylaminothiazolyl(lower)alkanoyl, more preferably lower alkanoylaminothiazolyl(lower)alkanoyl [e.g. 2-(2-formamidothiazol-4-yl)acetyl, etc.];
aminothiazolylglyoxyloyl [e.g. 2-(2-aminothiazol-4-yl)glyoxyloyl, etc.];
protected aminothiazolylglyoxyloyl, preferably acylaminothiazolylglyoxyloyl, more preferably lower alkanoylaminothiazolylglyoxyloyl [e.g. 2-(2-formamidothiazol-4-yl)glyoxyloyl, etc.];
ar(lower)alkanoyl having a lower alkoximino group, more preferably 2-lower alkoxyimino-2-phenylacetyl (e.g. 2-methoxyimino-2-phenylacetyl, 2-ethoxyimino-2-phenylacetyl, 2-propoxyimino-2-phenylacetyl, etc.);
aminothiazolyl(lower)alkanoyl having a hydroxyimino group, more preferably 2-hydroxyimino-2-aminothiazolacetyl [e.g. 2-hydroxyimino-2-(2-aminothiazol-4-yl)acetyl, etc.];
protected aminothiazolyl(lower)alkanoyl having a hydroxyimino group, preferably acylaminothiazolyl(lower)alkanoyl having a hydroxyimino group, more preferably 2-hydroxyimino-2-lower alkanoylaminothiazolylacetyl [e.g. 2-hydroxyimino-2-(2-formamidothiazol-4-yl)acetyl, etc.];
aminothiazolyl(lower)alkanoyl having a lower alkoxyimino group, more preferably 2-lower alkoxyimino-2-aminothiazolylacetyl [e.g. 2-methoxyimino-2-(2-aminothiazol-4-yl)-acetyl, 2-ethoxyimino-2-(2-aminothiazol-4-yl)acetyl, 2-propoxyimino-2-(2-aminothiazol-4-yl)acetyl, 2-isopropoxyimino-2-(2-aminothiazol-4-yl)acetyl, 2-butoxyimino-2-(2-aminothiazol-4-yl)acetyl, 2-pentyloxyimino-2-(2-aminothiazol-4-yl)acetyl, 2-hexyloxyimino-2-(2-aminothiazol-4-yl)acetyl, etc.];
protected aminothiazolyl(lower)alkanoyl having a lower alkoxyimino group, preferably acylaminothiazolyl(lower)alkanoyl having a lower alkoxyimino group, more preferably 2-lower alkoxyimino-2-lower alkanoylaminothiazolylacetyl [e.g. 2-methoxyimino-2-(2-formamidothiazol-4-yl)acetyl, 2p-ethoxyimino-2-(2-formamidothiazol-4-yl)acetyl, 2-propoxyimino-2-(2-formamidothiazol-4-yl)acetyl, 2-isopropoxyimino-2-(2-formamidothiazol-4-yl)acetyl, 2-butoxyimino-2-(2-formamidothiazol-4-yl)acetyl, 2-pentyloxyimino-2-(2-formamidothiazol-4-yl)acetyl, 2-hexyloxyimino-2-(2-formamidothiazol-4-yl)acetyl, etc.];
aminothiazolyl(lower)alkanoyl having a lower alkenyloxyimino group, more preferably 2-lower alkenyloxyimino-2-aminothiazolylacetyl [e.g. 2-vinyloxyimino-2-(2-aminothiazol-4-yl)acetyl, 2-allyloxyimino-2-(2-aminothiazol-4-yl)acetyl, etc.];
protected aminothiazolyl(lower)alkanoyl having a lower alkenyloxyimino group, preferably acylaminothiazolyl(lower)alkanoyl having a lower alkenyloxyimino group, more preferably 2-lower alkenyloxyimino-2-lower alkanoylaminothiazolylacetyl [e.g. 2-allyloxyimino-2-(2-formamidothiazol-4-yl)acetyl, etc.];
aminothiazolyl(lower)alkanoyl having a lower alkynyloxymino group, more preferably 2-lower alkynyloxyimino-2-aminothiazolylacetyl [e.g. 2-ethynyloxyimino-2-(2-aminothiazol-4-yl)acetyl, 2-(2-propynyloxyimino)-2-(2-aminothiazol-4-yl)acetyl, etc.];
protected aminothiazolyl(lower)alkanoyl having a lower alkynyloxyimino group, preferably acylaminothiazolyl(lower)alkanoyl having a lower alkynyloxyimino group, more preferably 2-lower alkynyloxyimino-2-lower alkanoylaminothiazolylacetyl [e.g. 2-(2-propynyloxyimino)-2-(2-formamidothiazol-4-yl)acetyl, etc.];

aminothiazolyl(lower)alkanoyl having an ar(lower)alkoxyimino group, more preferably 2-phenyl(lower)alkoxyimino-2-aminothiazolylacetyl [e.g. 2-benzyloxyimino-2-(2-aminothiazol-4-yl)acetyl, etc.];

protected aminothiazolyl(lower)alkanoyl having an ar(lower)alkoxyimino group, preferably acylaminothiazolyl(lower)alkanoyl having a phenyl(lower)alkoxyimino group, more preferably 2-phenyl(lower)alkoxyimino-2-lower alkanoylaminothiazolylacetyl [e.g. 2-benzyloxyimino-2-(2-formamidothiazol-4-yl)acetyl, etc.];

aminothiadiazolyl(lower)alkanoyl having a lower alkoxyimino group, more preferably 2-lower alkoxyimino-2-aminothiadiazolylacetyl [e.g. 2-methoxyimino-2-(5-amino-1,2,4-thiadiazol-3-yl)acetyl, 2-ethoxyimino-2-(5-amino-1,2,4-thiadiazol-3-yl)acetyl, 2-propoxyimino-2-(5-amino-1,2,4-thiadiazol-3-yl)acetyl, 2-hexyloxyimino-2-(5-amino-1,2,4-thiadiazol-3-yl)acetyl, etc.];

protected aminothiadiazolyl(lower)alkanoyl having a lower alkoxyimino group, preferably acylaminothiadiazolyl(lower)alkanoyl having a lower alkoxyimino group, more preferably 2-lower alkoxyimino-2-lower alkanoylaminothiadiazolylacetyl [e.g. 2-methoxyimino-2-(5-formamido-1,2,4-thiadiazol-3-yl)acetyl, etc.];

aminopyridyl(lower)alkanoyl having a lower alkoxyimino group, more preferably 2-lower alkoxyimino-2-aminopyridylacetyl [e.g. 2-methoxyimino-2-(6-aminopyridin-2-yl)acetyl, 2-ethoxyimino-2-(6-aminopyridin-2-yl)acetyl, 2-propoxyimino-2-(6-aminopyridin-2-yl)acetyl, etc.];

protected aminopyridyl(lower)alkanoyl having a lower alkoxyimino group, preferably acylaminopyridyl(lower)alkanoyl having a lower alkoxyimino group, more preferably 2-lower alkoxyimino-2-lower alkanoylaminopyridylacetyl [e.g. 2-methoxyimino-2-(6-formamidopyridin-2-yl)acetyl, etc.];

aminopyrimidinyl(lower)alkanoyl having a lower alkoxyimino group, more preferably 2-lower alkoxyimino-2-aminopyrimidinylacetyl [e.g. 2-methoxyimino-2-(4-aminopyrimidin-2-yl)acetyl, 2-ethoxyimino-2-(4-aminopyrimidin-2-yl)acetyl, 2-propoxyimino-2-(4-aminopyrimidin-2-yl)acetyl, etc.];

protected aminopyrimidinyl(lower)alkanoyl having a lower alkoxyimino group, preferably acylaminopyrimidinyl(lower)alkanoyl having a lower alkoxyimino group, more preferably 2-lower alkoxyimino-2-lower alkanoylaminopyrimidinylacetyl [e.g. 2-methoxyimino-2-(4-formamidopyrimidin-2-yl)acetyl, etc.];

dihydrooxathiinyl(lower)alkanoyl having a lower alkoxyimino group, more preferably 2-lower alkoxyimino-2-dihydrooxathiinylacetyl [e.g. 2-methoxyimino-2-(5,6-dihydro-1,4-oxathiin-2-yl)acetyl, 2-ethoxyimino-2-(5,6-dihydro-1,4-oxathiin-2-yl)acetyl, 2-propoxyimino-2-(5,6-dihydro-1,4-oxathiin-2-yl)acetyl, etc.]; and furyl(lower)alkanoyl having a lower alkoxyimino group, more preferably 2-lower alkoxyimino-2-furylacetyl [e.g. 2-methoxyimino-2-(2-furyl)acetyl, 2-ethoxyimino-2-(2-furyl)acetyl, 2-propoxyimino-2-(2-furyl)acetyl, etc.].

The processes for preparing the object compounds of the present invention are explained in detail in the following.

Process 1

The object compound (I) or a salt thereof can be prepared by subjecting the compound (II) or its reactive derivatives at the formyl group or a salt thereof to cyclization.

Suitable salt of the compound (II) may include an acid addition salt such as an organic acid salt (e.g. acetate, maleate, tartrate, benzenesulfonate, toluenesulfonate, etc.), or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivatives at the formyl group of the compound (II) may include all conventional reactive derivatives at the formyl group and reactive derivatives having equivalent workability to the compound (II) in this reaction. Suitable example of such reactive derivatives may include acetal (e.g. dimethyl acetal, diethyl acetal, etc.), hemiacetal, hydrate(diol), thioacetal, hemithioacetal, mono (or di)acylated diol and the like.

The present reaction, in case that the compound (II), in which $R^{3a}$ and $R^{3b}$ are linked together to form a group of the formula: $=P(R^5)_3$ wherein $R^5$ is as defined above, is used as the starting compound, is usually carried out in around neutral condition or in the presence of a base as mentioned hereinafter. The reaction is usually carried out in a solvent such as benzene, methylene chloride, dimethylsulfoxide, ethyl acetate, tetrahydrofuran or any other solvent which does not adversely affect the reaction. The reaction temperature is not critical, and the reaction is preferably carried out at ambient temperature or under warming.

In case that the compound (II), in which $R^{3a}$ is hydrogen and $R^{3b}$ is a group of the formula:

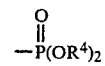

wherein $R^4$ is as defined above, is used as the starting compound, the present reaction is preferably carried out in the presence of a strong base such as alkali metal hydride (e.g. sodium hydride, lithium hydride, etc.), alkaline earth metal hydride (e.g. calcium hydride, etc.), alkali metal t-alkoxide (e.g. sodium t-butoxide, potassium t-butoxide, etc.), ar(lower)alkyl alkali metal (e.g. trityl sodium, trityl lithium, etc.), aryl alkali metal (e.g. phenyl lithium, etc.) or the like. The reaction is usually carried out in a solvent such as benzene, tetrahydrofuran, dioxane or any other solvent which does not adversely affect the reaction,. The reaction temperature is not critical, and the reaction is usually carried out at ambient temperature, under warming or heating.

Process 2

The object compound (I) or a salt thereof can be prepared by subjecting the compound (III) or its reactive derivatives at the hydroxymethyl group or a salt thereof to oxidation.

Suitable salt of the compound (III) can be referred to the ones exemplified as the salt of the compound (II).

Suitable reactive derivatives at the hydroxymethyl group of the compound (III) may include the compound wherein the hydroxymethyl group of the compound (III) is transformed into methyl group having an acid residue such as halogen (e.g. chlorine, bromine, etc.), arenesulfonyloxy (e.g. p-toluenesulfonyloxy, p-nitrobenzenesulfonyloxy, etc.), haloformyloxy (e.g. chloroformyloxy, etc.) or the like.

Suitable oxidizing agent to be used in this oxidation reaction may include conventional ones which can oxidize hydroxymethyl or reactive derivatives of the hydroxymethyl group to formyl.

In case that the starting compound has 2-hydroxyethoxy group at the 4th position of the azetidinone ring, said oxidizing agent may include (1) an activated dimethylsulfoxide formed by a reaction of dimethylsulfoxide and dicyclohexylcarbodiimide, dimethylsulfoxide and acetic anhydride, dimethylsulfoxide and phosphorus pentoxide, dimethylsulfoxide and sulfur trioxide-pyridine, dimethylsulfoxide and keteneimine, dimethylsulfoxide and chlorine, dimethylsulfoxide and mercuric acetate, dimethylsulfide and N-chlorosuccinimide, dimethylsulfide (or methylphenylsulfide) and chlorine, etc.; (2) chrome compound such as chromium trioxide-pyridine, chromium trioxide-sulfuric acid, alkali metal dichromate (e.g. sodium dichromate, potassium dichromate, etc.), lower alkyl chromate (e.g. t-butyl chromate, etc.) and the like.

The oxidation using dimethylsulfoxide and dicyclohexylcarbodiimide is preferably carried out in he presence of proton-donor such as an acid (e.g. phosphoric acid, trifluoroacetic acid, dichloroacetic acid, etc.), a mixture of acid and base (e.g. trifluoroacetic acid-pyridine, phosphoric acid-pyridine, etc.) or the like.

The present oxidation reaction is carried out without or in the presence of an acid or a base and it is optionally selected according to a kind of oxidizing agent to be used.

The present oxidation is carried out without or with solvent such as benzene, toluene, chloroform, methylene chloride, carbon tetrachloride, diethyl ether, dimethylformamide or any other solvent which does not adversely affect the reaction, and the solvent is optionally selected according to a kind of oxidizing agent to be used.

In case that the starting compound of the present oxidation reaction is in a form of reactive derivatives at the hydroxymethyl group, suitable oxidizing agent may include dimethylsulfoxide and the like. The present oxidation is preferably carried out in the presence of a base (e.g. sodium bicarbonate, triethylamine, etc.).

The reaction temperature of the oxidation reaction of this process is not critical, and the reaction is carried out under cooling, at ambient temperature, under warming or under heating. The reaction temperature is optionally selected according to a kind of oxidizing agent to be used.

By the present oxidation reaction, there is produced the compound of the formula (II) and said compound (II), without isolation, is immediately cyclized to give the object compound (I).

Process 3

The object compound (Ib) or a salt thereof can be prepared by subjecting the compound (Ia) or a salt thereof to deacylation reaction.

The present deacylation reaction is carried out in accordance with a conventional method such as hydrolysis; reduction; deacylation using Lewis acid; deacylation method by reacting the compound (Ia) with iminohalogenating agent and then with iminoetherifying agent, and, if necessary, subjecting the resulting compound to hydrolysis; or the like.

Among these methods, "the deacylation method by reacting the compound (Ia) with iminohalogenating agent and then with iminoetherifying agent, and, if necessary, subjecting the resulting compound to hydrolysis" is preferable method.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling.

In case that the compound (Ia) has a free carboxy group at the 4-position, this reaction is preferably carried out by protecting the free carboxy group with a sililating agent (e.g. trimethylsilyl chloride, trimethylsilylacetamide, bis(trimethylsilyl)acetamide, etc.) before this reaction.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions and kinds of the protective groups in the course of the reaction or in post-treatment. The hydrolysis may include a method using an acid or base and the like. These methods may be selected depending on the kind of the acyl groups to be eliminated.

Suitable acid may include an organic or an inorgaic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the deacylation reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,-2]octane, 1,5-diazabicyclo[5,4,0]undecene-5 or the like. The hydrolysis using a base is often carried out in water or a hydrophilic organic solvent or a mixed solvent thereof.

The reduction may include, for example, reduction with an alkali metal borohydride (e.g. sodium borohydride, etc.), catalytic reduction and the like.

The deacylation reaction using Lewis acid is carried out substantially in the same manner as described in Process 5.

Process 4

The object compound (Ia) or a salt thereof can be prepared by reacting the compound (Ib) or its reactive derivatives at the amino group or a salt thereof with an acylating agent. group of the compound (Ib) may include conventional ones such as Schiff's base type imino or its tautomeric enamine type derivatives formed by the reaction of the compound (Ib) with a carbonyl compound (e.g. aldehyde, ketone, etc.), isocyanate; a silyl derivatives formed by the reaction of the compound (Ib) with a silyl compound [e.g. bis(trimethylsilyl)acetamide, trimethylsilylacetamide, etc.]; a derivatives formed by reaction of the compound (Ib) with phosphorus trichloride or phosgene, or the like.

Suitable salt of the compound (Ib) can be referred to the ones exemplified for the compound (II).

The acylating agent to be used for the present reaction may include one of the formula:

$$R^{1a}\text{---OH} \qquad (XIV)$$

wherein $R^{1a}$ is defined above, or its reactive derivatives at the carboxy group or a salt thereof.

Suitable reactive derivatives at the carboxy group of the compound (XIV) may include an acid halide, an acid anhydride, an activated amide, an activated ester, and the like.

The suitable example may be an acid chloride;
an acid azide;
a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.);
a symmetrical acid anhydride;
an activated amide with imidazole, 4-substituted imidazole, dimethylpyrazole, triazole or tetrazole;
an activated ester [e.g. cyanomethyl ester, methoxymethyl ester, dimethyliminomethyl [(CH$_3$)$_2$N+ = CH—] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine], 1-hydroxy-2-(1H)pyridone, N-hydroxysuccinimide, N-hydroxyphthalimide or 1-hydroxy-6-chloro-1H-benzotriazole, and the like. These reactive derivatives at the carboxy group can optionally be selected from them according to the kind of the compound (XIV) to be used.

The salts of the compound (XIV) may be salts with an inorganic base such as an alkali metal salts (e.g. sodium or potassium salt) or an alkaline earth metal salt (e.g. calcium or magnesium salt), a salt with an organic base such as trimethylamine, triethylamine, dicyclohexylamine or the like.

The reaction of the compound (Ib) with the compound (XIV) is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound (XIV) is used in a free acid form or its salt form in the reaction, the reaction is preferably carried out in the presence of a conventional condensing agent such as carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonylbis(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vislmeier reagent [e.g. (chloromethylene) dimethylammonium chloride, a compound formed by the reaction of dimethylformamide with phosphorus oxychloride, etc.] or the like.

The reaction may also be carried out in the presence of an inorganic or an organic base such as an alkali metal bicarbonate, alkali metal carbonate, tri(lower)alkylamine, pyridine, N-(lower)alkylmorphorine, N,N-di(lower)alkylbenzylamine, N,N-di(lower)alkylaniline, or the like. When the base or the condensing agent is in liquid, it can be used also as a solvent. The reaction temperature is not critical, and the reaction is usually carried out under cooling or at ambient temperature.

In the present reaction, a syn isomer of the object compound (Ia) can be obtaned preferably by conducting the present reaction of the compound (Ib) with the syn isomer of the compound (XIV), for example, in the presence of a Vilsmeier reagent as mentioned above etc. and under around neutral condition.

Process 5

The object compound (Id) or a salt thereof can be prepared by subjecting the compound (Ic) or a salt thereof to elimination reaction of the carboxy protective group.

Suitable salt of the compound (Ic) can be referred to the acid addition salt exemplified for the compound (II).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the protective group of the carboxy and the elimination method.

The elimination using Lewis acid is preferable to eliminate substituted or unsubstituted ar(lower)alkyl ester and carried out by reacting the compound (Ic) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium carbon, Raney nickel, etc.).

The present elimination reaction of the carboxy protective group includes, within its scope, the cases that protected amino group in the compound (Ic) is transformed into free amino group according to reaction conditions and kinds of the protective groups in the course of the reaction and/or in post-treatment of the reaction.

Process 6

The object compound (If) or a salt thereof can be prepared by subjecting the compound (Ie) or a salt thereof to elimination reaction of the protective group of the amino.

Suitable salt of the compound (Ie) may include a metal salt, ammonium salt, an organic amine salt and the like as aforementioned.

The present elimination reaction is carried out in accordance with a conventional method such as hydrolysis; reduction; elimination using Lewis acid; Elimination method by reacting the compound (Ie) wherein the protective group is acyl group with iminohalogenating agent and then with iminoetherifying agent, and, if necessary, subjecting the resulting compound to hydrolysis; or the like.

The hydrolysis may include a method using an acid or base or hydrazine and the like. These methods may be selected depending on the kind of the protective groups to be eliminated.

Among these methods, hydrolysis using an acid is one of the commmon and preferable method for eliminating the protective group such as substituted or unsubstituted alkoxycarbonyl (e.g. t-pentyloxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), substituted phenylthio, substituted aralkylidene, substituted alkylidene, substituted cycloalkylidene, or the like. Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of protective group to be eliminated. When the elimination reaction is conducted with the acid, it can be carried out in the presence or absence of a solvent. Suitable solvent may include an organic solvent, water or a mixed solvent thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. trifluoroacetyl, etc.) etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5ene, 1,4-diazabicyclo[2,2,2]octane, 1,5-diazabicyclo[5,4,-

0]undecene-5 or the like. The hydrolysis using a base is often carried out in water or a hydrophilic organic solvent or a mixed solvent thereof.

Among the protective group, the acyl group can be generally eliminated by hydrolysis as mentioned above or by the other conventional hydrolysis. In case that the acyl group is halogen substitutedalkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.), catalytic reduction and the like.

The elimination reaction using Lewis acid is carried out substantially in the same manner as described in Process 5.

Suitable iminohalogenating agent used in a method as mentioned above may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling. Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may previously be added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may suitably be selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions etc. in the course of the reaction or in post-treatment.

In the aforementioned reactions in Processes 1 to 6 and/or the post-treating of the reactions of the present invention, the aforementioned geometrical isomer and/or tautomeric isomer may occasionally be transformed into the other geometrical isomer and/or tautomeric isomer and such cases are to be also included in the scope of the present invention.

In case that the object compound (Ia) has free carboxy group and/or free amino group, it may be transformed into its pharmaceutically acceptable salt as aforementioned by a conventional method.

The processes for preparing the starting compounds of the present invention are explained in detail in the following.

Suitable derivatives at the formyl group of the compounds (V)-(IX) and (XI)-(XIII) may include acetal (e.g. dimethyl acetal, diethyl acetal, etc.), hemiacetal, hydrate(diol), thioacetal, hemithioacetal, mono(or di)acylated diol and the like.

Suitable salts of the compounds (IV), (VI)-(IX) and (XI)-(XIII) can be referred to the ones as exemplified for the compound (II).

Preparation 1

The compound (VI) or its derivatives at the formyl group or a salt thereof can be prepared by reacting the compound (IV) or a salt thereof with the compound (V) or its derivatives at the formyl group.

The present reaction is preferably carried out in the presence of inorganic metal salt such as silver salts (e.g. silver tetrafluoroborate, silver oxide, silver perchlorate, etc.), stannic chloride, zinc chloride or the like.

The reaction is usually carried out in a solvent such as methylene chloride, toluene, chloroform or any other solvents which do not adversely affect the reaction.

The reaction temperature is not critical, and the reaction is preferably carried out under cooling or at ambient temperature.

Preparation 2

The compound (VII) or its derivatives at the formyl group or a salt thereof can be prepared by reacting the compound (VI) or its derivatives at the formyl group or a salt thereof with an acylating agent.

The present reaction can be carried out substantially in the same method as illustrated in Process 4.

The present acylation reaction includes, within its scope, the cases that the amino group and the hydroxy group in the compound (VI) are transformed into the corresponding acylated group according to the reaction conditions and kinds of the introduced group in the course of the reaction and/or in posttreatment of the reaction.

Preparation 3

The compound (VIII) or its derivatives at the formyl group or a salt thereof can be prepared by ozonolysis of the compound (VII) or its derivatives at the formyl group or a salt thereof, and if necessary, reducing the resulting compound.

The present reaction is usually carried out in a solvent such as ethyl acetate, methyl acetate or any other solvents which do not adversely affect the reaction.

The reaction temperature is not critical and the reaction is preferably carried out under cooling or at ambient temperature.

In case that the corresponding ozonide compound is produced in the present reaction, the compound (VIII) or its derivatives at the formyl group or a salt thereof can be obtained by further reducing the ozonide compound with a conventional reducing agent such as acid sodium sulfite, dimethyl sulfide trimethylphosphite or the like.

The present reaction is usually carried out in a solvent such as ethyl acetate or any other solvents which do not adversely affect the reaction.

The reaction temperature is not critical and the reaction is preferably carried out under cooling or at ambient temperature.

Preparation 4

The compound (IX) or its derivatives at the formyl group or a salt thereof can be prepared by subjecting the compound (VII) or its derivative at the formyl group or a salt thereof to oxidative cleavage reaction.

Suitable oxidizing agent used in the present oxidative cleavage reaction may include ozone, sodium dichromate, potassium permanganate and the like.

The present reaction is usually carried out in a solvent such as ethyl acetate, methyl acetate or any other solvents which do not adversely affect the reaction.

The reaction temperature is not critical and the reaction is preferably carried out under cooling or at ambient temperature.

Preparation 5

The compound (XI) or its derivatives at the formyl group or a salt thereof can be prepared by reducing the compound (VIII) or its derivatives at the formyl group or a salt thereof.

The present reduction can be carried out by a conventional method which is applied to the reduction of —CO— group to the corresponding —CH(OH)— group, for example, by using a combination of a metal (e.g. zinc, etc.) and an organic or inorganic acid (e.g. acetic acid, propionic acid, hydrochloric acid, etc.), lithium borohydride, sodium borohydride, aluminum amalgam; catalytic hydrogenation or the like.

The present reaction is preferably carried out in a solvent such as methylene chloride, tetrahydrofuran or any other solvents which do not adversely affect the reaction.

The reaction temperature is not critical and the reaction is preferably carried out under cooling at ambient temperature or under warming.

Preparation 6

The compound (XI) or its derivatives at the formyl group or a salt thereof can be prepared by reacting the compound (IX) or its derivatives at the formyl group or a salt thereof with the compound (X).

The present reaction is usually carried out in a solvent under anhydrous conditions. Suitable solvents are those such as benzene, toluene or any other solvents which do not adversely affect the reaction.

The reaction temperature is not critical and the reaction is preferably carried out under warming or heating.

Preparation 7

The compound (XII) or its derivatives at the formyl group or a salt thereof can be prepared by halogenating the compound (XI) or its derivatives at the formyl group or a salt thereof.

The present halogenation can be carried out by using a conventional halogenating agent such as phosphorus trihalide, phosphorus pentahalide, phosphorus oxychloride, thionyl halide and the like.

The present reaction may be carried out in the presence of a base such as lutidine, pyridine and the like.

The reaction is usually carried out in a solvent such as methylene chloride or any other solvents which do not adversely affect the reaction.

The reaction temperature is not critical and the reaction is preferably carried out under cooling, at ambient temperature or under warming.

Preparation 8

The compound (XIII) or its derivatives at the formyl group or a salt thereof can be prepared by reacting the compound (XII) or its derivatives at the formyl group or a salt thereof with a compound of the formula:

$$P(OR^4)_3 \text{ or } HP(OR^4)_2 \text{ or } P(R^5)_3$$

wherein $R^4$ and $R^5$ are each as defined above.

In case that

$$HP(OR^4)_2$$

is used in the present reaction, the present reaction is preferably carried out in the presence of an base as aforementioned.

The reaction is usually carried out in a solvent such as methylene chloride, benzene or any other solvents which do not adversely affect the reaction.

The reaction temperature is not critical and the reaction is preferably carried out at ambient temperature or under warming.

Preparation 9

The compound (III) or a salt thereof can be prepared by subjecting the compound (XIIIa) or a salt thereof to elimination reaction of the protective groups of the hydroxy.

The present elimination reaction is carried out in accordance with a conventional method such as hydrolysis and the like.

The hydrolysis is preferably carried out by using a base or an acid as illustrated in Process 6.

The reaction is usually carried out in a solvent such as methanol, ethanol, or any other solvents which do not adversely affect the reaction.

The reaction temperature is not critical and the reaction is preferably carried out under cooling, at ambient temperature or under warming.

Preparation 10

The compound (II) or a salt thereof can be prepared by oxidizing the compound (III) or a salt thereof.

The present reaction can be carried out substantially in the same method as illustrated in Process 2.

The object compound (Ia) of the present invention exhibits high antimicrobial activity and inhibits the growth of a number of microorganisms including pathogenic Gram-positive and Gram-negative bacteria.

For therapeutic administration, the cephalosporin analogues according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating infectious diseases caused by a number of pathogenic bacteria. In general amounts between 1 mg. and about 1000 mg. or even more may be administered per day.

Now, in order to show the utility of the object compounds (Ia), test data on anti-microbial activity of a representative compound of the present invention are shown below.

Test compound (1) 7β-[2-Methoxyimino-2-(2-aminothiazol-4-yl)acetamid]-1-oxadethia-3-cephem-4-carboxylic acid (syn isomer).
(2) 7β-[2-Ethoxyimino-2-(2-aminothiazol-4-yl)acetamido]-1-oxadethia-3-cephem-4-carboxylic acid (syn isomer).
(3) 7β-[2-Isopropoxyimino-2-(2-aminothiazol-4-yl)acetamido]-1-oxadethia-3-cephem-4-carboxylic acid (syn isomer).
(4) 7β-[2-Methoxyimino-2-(5-amino-1,2,4-thiadiazol-3-yl)acetamido]-1-oxadethia-3-cephem-4-carboxylic acid (syn isomer).
(5) 7β-[2-Methoxyimino-2-(4-aminopyrimidin-2-yl)acetamido]-1-oxadethia-3-cephem-4-carboxylic acid (syn isomer).

Test method

In vitro antibacterial activity was determined by the two-fold agar-plate dilution method as described below. One loopful of an overnight culture of each test strain in Trypticase-soy broth ($10^6$ viable cells per ml.) was streaked on heart infusion agar (HI-agar) containing graded concentrations of antibiotics, and the minimum inhibitory concentration (MIC) was expressed in terms of µg/ml after incubation at 37° C. for 20 hours.

| | Test result | | | | |
|---|---|---|---|---|---|
| | MIC (µg/ml) | | | | |
| | Compound | | | | |
| Test Bacteria | (1) | (2) | (3) | (4) | (5) |
| E. coli 31 | 0.05 | 0.05 | 0.20 | 0.025 | 0.025 |
| Kl. pneumoniae 20 | 0.10 | 0.025 | 0.05 | 0.05 | 0.05 |
| Pr. mirabilis 18 | 0.05 | 0.05 | 0.10 | 0.10 | 0.05 |
| Pr. vulgaris 2 | 0.2 | 0.05 | 0.10 | 0.10 | 0.10 |

Preferable starting compounds of the present invention can be represented by the following general formula.

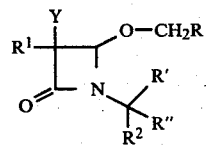
(XV)

wherein $R^1$ is amino or a substituted amino,
$R^2$ is carboxy or a protected carboxy,
R is hydroxymethyl, protected hydroxymethyl or formyl,
R' is hydrogen and R" is hydroxy, halogen or a group of the formula:

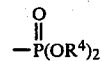

in which $R^4$ is lower alkyl, or R' and R" are linked together to form a group of the formula:

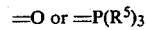

in which $R^5$ is lower alkyl, aryl or di(lower)alkylamino, and
Y is hydrogen or lower alkoxy, or a salt thereof.

The following examples are given for the purpose of illustrating the present invention:

EXAMPLE 1

(a) Preparation of the starting compound (1) Ethylene glycol (132.0 g.) was added to a solution of a mixture of 4α and 4β isomers of benzyl 2-(2-oxo-3β-amino-4-chloroazetidin-1-yl)-3-methyl-2-butenoate p-toluenesulfonate (118.2 g.) in methylene chloride (300 ml.). Silver oxide (68.5 g.) and silver tetrafluoroborate (57.6 g.) were in turn added thereto with stirring at −30° to −25° C. The resulting mixture was stirred for 30 minutes at −35° to −30° C. and then stirred for 40 minutes by gradually elevating the reaction temperature from −30° C. to 2° or 3° C. The reaction mixture was poured into benzene (2.0 l.), and a saturated aqueous solution of sodium bicarbonate (0.7 l.) and sodium chloride (80 g.) were added thereto under ice-cooling. The mixture was stirred for 30 minutes and filtered with celite. The organic layer was separated, washed twice with a saturated aqueous solution of sodium chloride (0.8 l.), dried over magnesium sulfate and concentrated under reduced pressure to give oil of a mixture of 4α and 4β isomers of benzyl 2-[2-oxo-3β-amino-4-(2-hydroxy-ethoxy)azetidin-1-yl]-3-methyl-2-butenoate (47.4 g.).

I.R. (Film): 3350, 1770, 1730 cm$^{-1}$.

N.M.R. (CDCl$_3$,δ): 2.00 (3H, s), 2.25 (3H, s), 3.10 (1H, broad s), 3.4–3.8 (4H, m), 5.1–5.6 (4H, m), 7.2–7.5 (5H, m).

(2) Pyridine (23.7 g.) was added at −30° C. to a solution of a mixture of 4α and 4β isomers of benzyl 2-[2-oxo-3β-amino-4-(2-hydroxy-ethoxy)azetidin-1-yl]-3-methyl-2-butenoate (47.4 g.) in methylene chloride (0.8 l.), and then phenoxy-acetyl chloride (51.15 g.) was added dropwise thereto. The resulting mixture was stirred for 1 hour at −30° to −20° C. and then for 30 minutes under ice-cooling. The reaction mixture was concentrated under reduced pressure, and then ethyl acetate (1 l.) and 0.5 N hydrochloric acid (0.4 ) were added to the residue. The organic layer was separated, washed with a saturated aqueous solution of sodium chloride (0.3 l.), dried over magnesium sulfate and concentrated under reduced pressure to give oil (83.8 g.). The oil was subjected to column chromatography on silica gel (2.0 kg.) and eluted with a mixture of benzene and ethyl acetate (5:1 or 3:1) to first give benzyl 2-[2- oxo-3β-phenoxyacetamido-4α-(2-phenoxyacetoxyethoxy)azetidin-1-yl]-3-methyl-2-butenoate (1.1 g.).

I.R. (CH$_2$Cl$_2$): 3400, 1770, 1720, 1690 cm$^{-1}$.

N.M.R. (CDCl$_3$, δ): 2.02 (3H, s), 2.25 (3H, s), 3.65–3.95 (2H, m), 4.10–4.40 (2H, m), 4.50 (2H, s), 4.63 (2H, s), 5.00–5.45 (4H, m), 6.85–7.50 (15H or 16H, m).

And then, from the subsequent fractions, a mixture of 4α and 4β isomers of benzyl 2-[2-oxo-3β-phenoxyacetamide-4-(2-phenoxyacetoxyethoxy)azetidin-1-yl]-3-methyl-2-butenoate (19.4 g.) was obtained.

Further, from the following fractions, benzyl 2-[2-oxo-3β-phenoxyacetamido-4β-(2-phenoxyacetoxyethoxy)azetidin-1-yl]-3-methyl-2-butenoate (17.2 g.) was obtained.

I.R. (CH$_2$Cl$_2$): 3400, 1770, 1720, 1690 cm$^{-1}$.

N.M.R. (CDCl$_3$, δ): 2.00 (3H, s), 2.25 (3H, s), 3.5–3.75 (2H, m), 4.0–4.3 (2H, m), 4.55 (4H, s), 5.15-5.52 (4H, m), 6.75–7.50 (15H or 16H, m).

(3) (i) Ozone gas was passed for 1 hour at −60° to −62° C. into a solution of benzyl 2-[2-oxo-3β-phenoxyacetamido-4β-(2-phenoxyacetoxyethoxy)azetidin-1-yl]-3-methyl-2-butenoate (16.3 g.) in ethyl acetate (165 ml.). The mixture was elevated to a temperature of ice-cooling, and ethyl acetate (160 ml.) and a solution of sodium bisulfite (28.1 g.) and sodium sulfite (7.0 g.) in water (280 ml.) were added thereto. After stirring for 5 minutes, the organic layer was separated. The organic layer was washed with a saturated aqueous solution of sodium chloride (100 ml.), dried over magnesium sulfate and concentrated under reduced pressure to give oil (16.1 g.). The oil was crystallized with a mixture of diethyl ether and methanol (10:1) (120 ml.) to give crystals of benzyl 2-[2-oxo-3β-phenoxyacetamido-4β-(2-phenoxyacetoxyethoxy)azetidin-1-yl]glyoxylate (10.0 g.). From the mother liquor, the same compound (0.71 g.) was obtained, mp 102° to 103° C. (dec.).

I.R. (Nujol): 3380, 1810, 1750, 1735, 1710, 1670 cm$^{-1}$.

N.M.R. (CDCl$_3$, δ): 3.92–4.40 (4H, m), 4.56 (2H, s), 4.59 (2H, s), 5.35 (2H, s), 5.50–5.77 (2H, m), 7.80–8.50 (15H or 16H, m).

(ii) Ozone gas was passed for 80 minutes at −60° to −64° C. into a solution of a mixture of 4α and 4β isomers of benzyl 2-[2-oxo-3β-phenoxyacetamido-4-(2-phenoxyacetoxyethoxy)azetidin-1-yl]-3-methyl-2-butenoate (18.0 g.) in ethyl acetate (180 ml.), and then a solution of sodium bisulfite (31.1 g.) and sodium sulfite (8.0 g.) in water (300 ml.) was added thereto. The organic layer was separated, washed with a saturated aqueous solution of sodium chloride, dried over magnesium sulfate and concentrated under reduced pressure to give oil (16.1 g.). The oil was crystallized with a mixture of diethyl ether and methanol (10:1) (80 ml.) to give crystals, which was collected by filtration to give crystals of benzyl-2-[2-oxo-3β-phenoxyacetamido-4β-)2-phenoxyacetoxyethoxy)azetidin-1-yl]glyoxylate (5.96 g.), mp 103° C. (dec.).

(iii) Ozone gas was passed for 15 minutes at −55° to −60° C. into a solution of benzyl 2-[2-oxo-3β-phenoxyacetamido-4β-(2-phenoxyacetoxyethoxy)azetidin-1-yl]-3-methyl-2-butenoate (3.0 g.) in methyl acetate (60 ml.). The reaction mixture was poured into a mixture of ethyl acetate (300 ml.) and a solution of sodium bisulfite (9.0 g.) and sodium hydroxide (1.1 g.) in water (100 ml.). The ethyl acetate layer was separated, washed with water, dried over magnesium sulfate and concentrated under reduced pressure to give oil (2.76 g.). The oil was dissolved in methanol (40 ml.) and the solution was stirred for 1 hour at ambient temperature, which was concentrated under reduced pressure to give oil (3.2 g.). The oil was subjected to column chromatography on silica gel (30 g.) and eluted with chloroform or a mixture of chloroform and ethyl acetate (1:1) to give oil of 2-oxo-3β-phenoxyacetamido-4β-(2-phenoxyacetoxyethoxy)azetidine (970 mg.). The oil was crystallized with a mixture of diethyl ether and methanol (10:1) to give crystals of the same compound (800 mg.), mp 100° to 102° C. (dec.).

Mass (m/e): 414 (M$^+$).

I.R. (Nujol): 3380, 3200, 1785, 1760, 1720, 1660 cm$^{-1}$.

N.M.R. (CDCl$_3$, δ): 3.72 (2H, t, J=5 Hz), 4.31 (2H, m), 4.54 (2H, s), 4.64 (2H, s), 5.07 (1H, d, J=4 Hz), 5.45 (1H, dd, J=4, 10 Hz), 6.85–7.50 (12H, m).

(iv) Ozone gas was passed for 60 minutes at −60° to −62° C. into a solution of a mixture of 4α and 4β isomers of benzyl 2-[2-oxo-3β-phenoxyacetamido-4-(2-phenoxyacetoxyethoxy)azetidin-1-yl]-3-methyl-2-butenoate (20.88 g.) in methyl acetate (400 ml.). The reaction mixture was elevated to a temperature of ice-cooling and poured into a mixture of ethyl acetate (2.0 l.) and a solution of sodium bisulfite (63.0 g.) and sodium hydroxide (7.8 g.) in water (600 ml.). The ethyl acetate layer was separated, washed with a saturated aqueous solution of sodium chloride (1.0 l.), dried over magnesium sulfate and concentrated under reduced pressure to give oil (19.1 g.). The oil was dissolved in methanol (400 ml.) and the solution was stirred for 1 hour at ambient temperature, which was concentrated under reduced pressure to give oil (17.0 g.). The oil was subjected to column chromatography on silica gel (350 g.) and eluted with a mixture of benzene and ethyl acetate (2:3 or 1:2) to give oil of 2-oxo-3β-phenoxyacetamido-4β-(2-phenoxyacetoxyethoxy)azetidine (3.65 g.). The oil was crystallized with a mixture of diethyl ether and methanol (10:1) (60 ml.) to give crystals of the same compound (2.27 g.). This compound was identified with the compound obtained in Example 1 (a) (3) (iii) by melting point, I.R. and N.M.R. spectra.

(4) (i) Zinc powder (5.50 g.) was added under ice-cooling to a solution of benzyl 2-[2-oxo-3β-phenoxyacetamido-4β-(2-phenoxyacetoxyethoxy)azetidin-1-yl]glyoxylate (5.50 g.) in a mixture of methylene chloride (27.5 ml.) and acetic acid (27.5 ml.). The resulting mixture was stirred for 1 hour at the same temperature and for 30 minutes at ambient temperature. Zinc powder was filtered off with celite and the celite layer was washed three times with ethyl acetate (10 ml.). The filtrate and the washings were combined and poured into ethyl acetate (150 ml.). The ethyl acetate layer was in turn washed with water (70 ml.), 5% aqueous solution of sodium bicarbonate (70 ml.) and water (50 ml.×2), dried over magnesium sulfate and concentrated under reduced pressure to give foamy powder of benzyl 2-[2-oxo-3β-phenoxyacetamido-4β-(2-phenoxyacetoxyethoxy)azetidin-1-yl]glycolate (a mixture of epimers at 2 position) (5.50 g.).

I.R. (CH$_2$Cl$_2$): 3410, 1780, 1740, 1690 cm$^{-1}$.

(ii) Benzene (40 ml.) was added to 2-oxo-3β-phenoxyacetamido-4β-(2-phenoxyacetoxyethoxy)azetidine (414 mg.), and t-butyl glyoxylate monohydrate (1.48 g.) was added thereto. The resulting mixture was refluxed for 23 hours. The reaction mixture was washed with water, dried over magnesium sulfate and concentrated under reduced pressure to give oil of t-butyl 2-[2-oxo-3β-phenoxyacetamido-4β-(2-phenoxyacetoxyethoxy)azetidin-1-yl]glycolate (a mixture of epimers at 2 position) (680 mg.).

I.R. (CHCl$_3$): 3500, 3420, 1780, 1735, 1690 cm$^{-1}$.

N.M.R. (CDCl$_3$, δ): 1.45 (9H, s), 3.5–3.9 (2H, m), 4.0–4.4 (2H, m), 4.50 (2H, s), 4.58 (2H, s), 5.17 (1H, d, J=4 Hz), 5.27 (1H, s), 5.45 (1H, dd, J=4, 9 Hz), 6.75–7.45 (11H, m)

(5) 2,6-Lutidine (3.10 g.) was added under ice-cooling to a solution of benzyl 2-[2-oxo-3β-phenoxyacetamido-4β-(2-phenoxyacetoxyethoxy)azetidin-1-yl]glycolate (a mixture of epimers at 2 position)(5.50 g.) in methylene chloride (100 ml.), and then a solution of thionyl chloride (3.45 g.) in methylene chloride (5 ml.) was added dropwise thereto. After stirring for 45 minutes under ice-cooling, the reaction mixture was washed twice with a cold aqueous solution of sodium chloride (50 ml.), dried over magnesium sulfate and concentrated under reduced pressure to give foamy powder of benzyl 2-chloro-2-[2-oxo-3β-phenoxyacetamido-4β-(2-phenoxyacetoxyethoxy)azetidin-1-yl]acetate (a mixture of epimers at 2 position) (5.90 g.).

I.R. (CH$_2$Cl$_2$): 3400, 1790, 1760, 1690 cm$^{-1}$.

(6) Triphenylphosphine (3.80 g.) was added to a solution of benzyl 2-chloro-2-[2-oxo-3β-phenoxyacetamido-4β-(2-phenoxyacetoxyethoxy)azetidin-1-yl]acetate (a mixture of epimers at 2 position (5.90 g.) in methylene chloride (60 ml.), and the resulting mixture was refluxed for 2 hours in a stream of nitrogen gas. The reaction mixture was poured into ethyl acetate (300 ml.). The mixture was in turn washed with 5% aqueous solution of sodium bicarbonate (50 ml.) and water (50 ml.×2), dried over magnesium sulfate and concentrated under reduced pressure to give foamy substance (8.80 g.). This substance was subjected to column chromatography on silica gel (90 g.) and eluted with a mixture of benzene and ethyl acetate (1:1) to give foamy powder of benzyl 2-triphenylphosphoranylidene-2-[2-oxo-3β-phenoxyacetamido-4β-(2-phenoxyacetoxyethoxy)azetidin-1-yl]acetate (4.84 g.).

I.R. (CHCl$_3$): 3400, 1760, 1680 cm$^{-1}$.

N.M.R. (CDCl$_3$, δ) 3.5–3.8 (2H, m), 3.9–4.1 (2H, m), 4.44 (4H, s), 4.5–4.9 (2H, m), 5.0–5.3 (2H, m).

(7) An 1 N aqueous solution of sodium hydroxide (1 ml.) was added under ice-cooling to a solution of benzyl 2-triphenylphosphoranylidene-2-[2-oxo-3β-phenoxyacetamido-4β-(2-phenoxyacetoxyethoxy)azetidin-1-yl]acetate (1.50 g.) in a mixture of methanol (40 ml.) and water (10 ml.). The resulting mixture was stirred for 15 minutes under ice-cooling and for 1.5 hours at ambient temperature. The reaction mixture was concentrated to a volume of about 20 ml., and ethyl acetate (100 ml.) was added thereto. The ethyl acetate layer was in turn washed with 5% aqueous solution of sodium bicarbonate (20 ml.) and water (30 ml.), dried over magnesium sulfate and concentrated under reduced pressure to give oil (1.42 g.). The oil was subjected to column chromatography on silica gel (15 g.) and eluted with ethyl acetate to give foamy powder of benzyl 2-triphenylphosphoranylidene-2-[2-oxo-3β-phenoxyacetamido-4β-(2-hydroxyethoxy)azetidin-1-yl]acetate (960 mg.).

I.R. (CHCl$_3$): 3400, 1760, 1740, 1680 cm$^{-1}$.

N.M.R. (CDCl$_3$, δ): 3.2–3.7 (4H, m), 4.24 (2H, s), 4.76 (2H, s), 4.9–5.2 (2H, m).

(b) Preparation of the object compound (1) Dicyclohexylcarbodiimide (310 mg.) and pyridine (40 mg.) were added to a mixture of dimethylsulfoxide (1.5 ml.) and benzene (3 ml.), and then benzyl 2-triphenylphosphoranylidene-2-[2-oxo-3β-phenoxyacetamido-4β-(2-hydroxyethoxy)azetidin-1-yl]acetate (344 mg.) was added thereto with stirring. To the mixture was added dropwise a solution of trifluoroacetic acid (28 mg.) in benzene (0.2 ml.), and the resulting mixture was stirred for 14 hours at ambient temperature. In the course of the reaction, benzyl 2-triphenylphosphoranylidene-2-(2-oxo-3β-phenoxyacetamido-4β-formylmethoxyazetidin-1-yl)acetate was produced, and immediately cyclized to give the object compound, which was purified as follows.

Benzene (30 ml.) was added to the reaction mixture, and insoluble material was filtered off. The The filtrate was in turn washed with 1% hydrochloric acid (10 ml.), water (10 ml.), 5% aqueous solution of sodium bicarbonate (10 ml.) and water (10 ml.×2). The organic layer was dried over magnesium sulfate and concentrated under reduced pressure to give oil (380 mg.). The oil was subjected to column chromatography on silica gel (8 g.) and eluted with a mixture of benzene and ethyl acetate (1:1) to give powder of benzyl 7β-phenoxyacetamido-1-oxadethia-3-cephem-4-carboxylate (173 mg.).

I.R. (CHCl$_3$): 3420, 1795, 1725, 1690 cm$^{-1}$.

N.M.R. (CDCl$_3$, δ): 4.52 (4H, broad s), 5.06 (1H, d, J=4 Hz), 5.28 (2H, s), 5.76 (1H, dd, J=4, 10 Hz), 6.50 (1H, t, J=2 Hz), 6.9–7.5 (11H, m).

(2) Benzyl 2-triphenylphosphoranylidene-2-[2-oxo-3β-phenoxyacetamido-4β-(2-hydroxyethoxy)azetidin-1-yl]acetate (180 mg.) was dissolved in a mixture of dimethylsulfoxide (1.8 ml.) and acetic anhydride (1.8 ml.), and the solution was stirred for 15 hours at ambient temperature in a stream of nitrogen gas. In the course of the reaction, benzyl 2-triphenylphosphoranylidene-2-(2-oxo-3β-phenoxyacetamido-4β-formylmethoxyazetidin-1-yl)acetate was produced and then cyclized. The reaction mixture was concentrated under reduced pressure to about half volume and benzene was added to the residue. The mixture was washed with water, dried over magnesium sulfate and concentrated under reduced pressure to give oil (200 mg.), which was purified by preparative thin-layer chromatography to give benzyl 7β-phenoxyacetamido-1-oxadethia-3-cephem-4-carboxylate. This compound was identified with the compound obtained in Example 1 (b) (i) by I.R. spectrum.

(3) A solution of benzyl 2-triphenylphosphoranylidene-2-[2-oxo-3β-phenoxyacetamido-4β-(2-hydroxyethoxy)azetidin-1-yl]acetate (200 mg.) in methylene chloride (4 ml.) was added under ice-cooling and stirring to a solution of chromium trioxide-pyridine complex (465 mg.) in methylene chloride (9 ml.). After stirring for 1 hour, chromium trioxide-pyridine complex (470 mg.) was added thereto and the mixture was stirred for 30 minutes. In the course of the reaction, benzyl 2-triphenylphosphoranylidene-2-(2-oxo-3β-phenoxyacetamido-4β-formylmethoxyazetidin-1-yl)acetate was produced and cyclized to give the object compound. The reaction mixture was in turn washed with 5% hydrochloric acid, 5% aqueous solution of sodium bicarbonate and water, dried over magnesium sulfate and concentrated under reduced pressure to give oil (150 mg.), which was purified by preparative thin-layer chromatography using a mixture of benzene and ethyl acetate (2:1) as a developing solvent to give benzyl 7β-phenoxyacetamido-1-oxadethia-3-cephem-4-carboxylate. This compound was identified with the compound obtained in Example 1 (b) (i) by I.R. spectrum.

EXAMPLE 2

The following compounds were prepared according to the similar manner to that of Example 1.

(1) Benzyl 7β-amino-1-oxadethia-3-cephem-4-carboxylate, oil.
   I.R. (CHCl₃): 3350, 1785, 1720 cm⁻¹.

(2) Benzyl 7β-amino-1-oxadethia-3-cephem-4-carboxylate p-toluenesulfonate, mp 148° to 153° C. (dec.).

(3) 7β-Amino-1-oxadethia-3-cephem-4-carboxylic acid.
   I.R. (Nujol): 2700–2270, 2120, 1805, 1630, 1540, 1505 cm⁻¹.

(4) Benzyl 7α-methoxy-7β-amino-1-oxadethia-3-cephem-4-carboxylate, oil.
   I.R. (CH₂Cl₂): 1785, 1725 cm⁻¹.

(5) Benzyl 7β-[2-methoxyimino-2-(2-formamidothiazol-4-yl)acetamido]-1-oxadethia-3-cephem-4-carboxylate (syn isomer) powder.
   I.R. (Nujol): 3250, 1795, 1725, 1690, 1680 cm⁻¹.

(6) Benzyl 7β-[2-ethoxyimino-2-(2-formamidothiazol-4-yl)acetamido]-1-oxadethia-3-cephem-4-carboxylate (syn isomer) mp 120° C.

(7) Benzyl 7β-[2-isopropoxyimino-2-(2-formamidothiazol-4-yl)acetamido]-1-oxadethia-3-cephem-4-carboxylate (syn isomer), crystal, mp 162° to 166° C.

(8) Benzyl 7β-[2-methoxyimino-2-(6-formamidopyridin-2-yl)acetamido]-1-oxadethia-3-cephem-4-carboxylate (syn isomer), which was decomposed up to 170° C.

(9) Benzyl 7β-[D,L-2-sulfo-2-phenylacetamido]-1-oxadethia-3-cephem-4-carboxylate, amorphous solid.
   I.R. (CH₂Cl₂): 3280, 1790, 1720, 1670, 1635 cm⁻¹.

(10) Benzyl 7β-[2-methoxyimino-2-(4-aminopyrimidin-2-yl)acetamido]-1-oxadethia-3-cephem-4-carboxylate (syn isomer), mp 120° to 137° C.

(11) Benzyl 7β-[2-methoxyimino-2-(5-amino-1,2,4-thiadiazol-3-yl)acetamido]-1-oxadethia-3-cephem-4-carboxylate (syn isomer)
   I.R. (Nujol): 3450, 3360, 3240, 1790, 1735, 1675 cm⁻¹.

(12) Benzyl 7β-[2-n-butoxyimino-2-(2-formamidothiazol-4-yl)acetamido]-1-oxadethia-3-cephem-4-carboxylate (syn isomer).
   I.R. (Nujol): 1780, 1720, 1670, 1630 cm⁻¹.

(13) Benzyl 7β-[2-n-pentyloxyimino-2-(2-formamidothiazol-4-yl)acetamido]-1-oxadethia-3-cephem-4-carboxylate (syn isomer), mp 136° to 147° C.

(14) Benzyl 7β-(2-methoxyimino-2-phenylacetamido)-1-oxadethia-3-cephem-4-carboxylate (syn isomer), mp 157° to 158.5° C.

(15) Benzyl 7β-[2-(2-formamidothiazol-4-yl)glyoxylamido]-1-oxadethia-3-cephem-4-carboxylate, mp 220° to 221° C. (dec.).

(16) Benzyl 7β-[2-methoxyimino-2-(5,6-dihydro-1,4-oxathiin-2-yl)acetamido]-1-oxadethia-3-cephem-4-carboxylate (syn isomer).
   I.R. (Nujol): 3400, 1795, 1725, 1680, 1640 cm⁻¹.

(17) Benzyl 7β-[2-(1H-1,2,3,4-tetrazol-1-yl)acetamido]-1-oxadethia-3-cephem-4-carboxylate, mp 181° to 183° C.

(18) Benzyl 7β-[2-methoxyimino-2-(2-furyl)acetamido]-1-oxadethia-3-cephem-4-carboxylate (syn isomer).
   I.R. (Nujol): 3390, 1795, 1730, 1690, 1635 cm⁻¹.

(19) 7β-[2-Ethoxyimino-2-(2-aminothiazol-4-yl)acetamido]-1-oxadethia-3-cephem-4-carboxylic acid (syn isomer), which is gradually decomposed from 150° C.

(20) 7β-[2-Isopropoxyimino-2-(2-formamidothiazol-4-yl)acetamido]-1-oxadethia-3-cephem-4-carboxylic acid (syn isomer), mp 171° to 210° C. (dec.).

(21) 7β-[2-Isopropoxyimino-2-(2-aminothiazol-4-yl)acetamido]-1-oxadethia-3-cephem-4-carboxylic acid hydrochloride (syn isomer), which is softened at 65° to 70° C. and gradually decomposed up to 140° C.

(22) 7β-[2-n-Butoxyimino-2-(2-formamidothiazol-4-yl)acetamido]-1-oxadethia-3-cephem-4-carboxylic acid (syn isomer), which is decomposed up to 165° C.

(23) 7β-[2-n-Butoxyimino-2-(2-aminothiazol-4-yl)acetamido]-1-oxadethia-3-cephem-4-carboxylic acid (syn isomer), dp>200° C.

(24) 7β-[2-n-Pentyloxyimino-2-(2-formamidothiazol-4-yl)acetamido]-1-oxadethia-3-cephem-4-carboxylic acid (syn isomer), mp 142° to 147° C. (dec.).

(25) 7β-[2-n-Pentyloxyimino-2-(2-aminothiazol-4-yl)acetamido]-1-oxadethia-3-cephem-4-carboxylic acid hydrochloride (syn isomer) (powder), mp 118° to 124° C. (dec.).

(26) 7β-[2-Methoxyimino-2-(6-formamidopyridin-2-yl)acetamido]-1-oxadethia-3-cephem-4-carboxylic acid (syn isomer), mp 130° to 160° C. (dec.).

(27) 7β-[2-Methoxyimino-2-(6-aminopyridin-2-yl)acetamido]-1-oxadethia-3-cephem-4-carboxylic acid hydrochloride (syn isomer) (powder), mp 100° to 140° C. (dec.).

(28) 7β-(2-Methoxyimino-2-phenylacetamido)-1-oxadethia-3-cephem-4-carboxylic acid (syn isomer), mp 80° to 95° C. (dec.).

(29) 7β-[2-(2-Formamidothiazol-4-yl)glyoxylamido]-1-oxadethia-3-cephem-4-carboxylic acid, mp 200° to 220° C. (dec.).

(30) 7β-[2-(2-Aminothiazol-4-yl)glyoxylamido]-1-oxadethia-3-cephem-4-carboxylic acid, dp>240° C.

(31) 7β-[2-(1H-1,2,3,4-Tetrazol-1-yl)acetamido]-1-oxadethia-3-cephem-4-carboxylic acid, mp 164° to 167° C. (dec.).

(32) 7β-[2-Methoxyimino-2-(2-furyl)acetamido]-1-oxadethia-3-cephem-4-carboxylic acid (syn isomer), mp 197° C. (dec.).

(33) 7β-[2-Methoxyimino-2-(5,6-dihydro-1,4-oxathiin-2-yl)acetamido]-1-oxadethia-3-cephem-4-carboxylic acid (anti isomer), mp 163° to 165° C. (dec.).

(34) 7β-(D,L-2-sulfo-2-phenylacetamido)-1-oxadethia-3-cephem-4-carboxylic acid (amorphous solid).
   I.R. (KBr): 1790, 1730, 1680 cm⁻¹.

(35) 7β-Phenoxyacetamido-1-oxadethia-3-cephem-4-carboxylic acid, mp 174° to 176° C.

(36) 7β-[2-Methoxyimino-2-(2-formamidothiazol-4-yl)acetamido]-1-oxadethia-3-cephem-4-carboxylic acid (syn isomer).
   I.R. (Nujol): 3600–2200, 1780, 1720, 1670 cm⁻¹.

(37) 7β-[2-Methoxyimino-2-(2-aminothiazol-4-yl)acetamido]-1-oxadethia-3-cephem-4-carboxylic acid hydrochloride (syn isomer).
   I.R. (Nujol): 3400–2400, 1780, 1730, 1680, 1640 cm⁻¹.

(38) 7β-[2-Methoxyimino-2-(2-aminothiazol-4-yl)acetamido]-1-oxadethia-3-cephem-4-carboxylic acid (syn isomer), powder.
   I.R. (Nujol): 3600–2400, 1785, 1720, 1660 cm⁻¹.

(39) Benzyl 7β-[2-allyloxyimino-2-(2-formamidothiazol-4-yl)acetamido]-1-oxadethia-3-cephem-4-carboxylate (syn isomer), amorphous solid.
   I.R. (CH₂Cl₂): 3370, 3250–3020, 1790, 1720, 1680, 1630 cm⁻¹.

(40) Benzyl 7β-[2-{2-propynyloxyimino}-2-(2-formamidothiazol-4-yl)acetamido]-1-oxadethia-3-cephem-4-carboxylate (syn isomer).

I.R. (CH₂Cl₂): 3380, 3290, 1790, 1720, 1680, 1635, 1540 cm⁻¹.

(41) Benzyl 7β-[2-benzyloxyimino-2-(2-formamidothiazol-4-yl)acetamido]-1-oxadethia-3-cephem-4-carboxylate (syn isomer).

I.R. (CH₂Cl₂): 3350, 3270-3120, 1790, 1720, 1680, 1630, 1540 cm⁻¹.

(42) 7β-[2-Methoxyimino-2-(4-aminopyrimidin-2-yl)acetamido]-1-oxadethia-3-cephem-4-carboxylic acid (syn isomer), crystal.

I.R. (Nujol): 3460, 3350, 3260, 1780, 1630 cm⁻¹.

(43) 7β-[2-Methoxyimino-2-(5-amino-1,2,4-thiadiazol-3-yl)acetamido]-1-oxadethia-3-cephem-4-carboxylic acid (syn isomer), powder.

I.R. (Nujol): 3400, 3350, 3260, 1780, 1700, 1640 cm⁻¹.

(44) 7β-[2-Allyloxyimino-2-(2-formamidothiazol-4-yl)acetamido]-1-oxadethia-3-cephem-4-carboxylic acid (syn isomer).

I.R. (Nujol): 3450, 3330, 3170, 1770, 1690, 1645, 1635, 1620, 1540 cm⁻¹.

(45) 7β-[2-(2-Propynyloxyimino)-2-(2-formamidothiazol-4-yl)acetamido]-1-oxadethia-3-cephem-4-carboxylic acid (syn isomer).

I.R. (Nujol): 3250, 1780, 1720, 1680, 1660 cm⁻¹.

(46) 7β-[2-Benzyloxyimino-2-(2-formamidothiazol-4-yl)acetamido]-1-oxadethia-3-cephem-4-carboxylic acid (syn isomer), crystalline solid.

I.R. (Nujol): 3250, 1780, 1670, 1540 cm⁻¹.

(47) 7β-[2-Allyloxyimino-2-(2-aminothiazol-4-yl)acetamido]-1-oxadethia-3-cephem-4-carboxylic acid (syn isomer).

I.R. (Nujol): 3300, 1780, 1660, 1540 cm⁻¹.

(48) 7β-[2-(2-Propynyloxyimino)-2-(2-aminothiazol-4-yl)acetamido]-1-oxadethia-3-cephem-4-carboxylic acid hydrochloride (syn isomer) which is gradually decomposed with coloration till 160° C.

(49) 7β-[2-Benzyloxyimino-2-(2-aminothiazol-4-yl)acetamido]-1-oxadethia-3-cephem-4-carboxylic acid (syn isomer), mp 150° to 170° C. (gradually decomposed with coloration).

(50) Benzyl 7β-[2-methoxyimino-2-(5,6-dihydro-1,4-oxathiin-2-yl)acetamido]-1-oxadethia-3-cephem-4-carboxylate (anti isomer), mp 142° to 144° C.

(51) Benzyl 7α-methoxy-7β-[2-methoxyimino-2-(2-formamidothiazol-4-yl)acetamido]-1-oxadethia-3-cephem-4-carboxylate (syn isomer), amorphous solid.

I.R. (CH₂CCl₂): 3350, 1780, 1720, 1690 cm⁻¹.

(52) Benzyl 7α-methoxy-7β-[2-(2-formamidothiazol-4-yl)acetamido]-1-oxadethia-3-cephem-4-carboxylate.

I.R. (CH₂CCl₂): 3350, 1780, 1720, 1690 cm⁻¹.

(53) 7α-Methoxy-7β-[2-methoxyimino-2-(2-formamidothiazol-4-yl)acetamido]-1-oxadethia-3-cephem-4-carboxylic acid (syn isomer), amophous solid.

N.M.R. (acetone-d₆, δ): 3.58 (3H, s), 3.97 (3H, s), 4.68 (2H, m), 5.16 (1H, s), 6.40 (1H, t, J=3 Hz), 7.60 (1H, s), 8.70 (1H, s), 8.75 (1H, s).

(54) 7α-Methoxy-7β-[2-(2-formamidothiazol-4-yl)acetamido]-1-oxadethia-3-cephem-4-carboxylic acid, amorphous solid.

I.R. (Nujol): 3290, 3150, 1765, 1680 cm⁻¹.

(55) 7α-Methoxy-7β-[2-methoxyimino-2-(2-aminothiazol-4-yl)acetamido]-1-oxadethia-3-cephem-4-carboxylic acid hydrochloride (syn isomer).

I.R. (Nujol): 1780, 1720, 1680, 1630 cm⁻¹.

(56) 7α-Methoxy-7β-[2-(2-aminothiazol-4-yl)acetamido]-1-oxadethia-3-cephem-4-carboxylic acid hydrochloride, powder.

I.R. (KBr): 1780, 1700, 1630 cm⁻¹.

(57) 7β-[2-ethoxyimino-2-(2-formamidothiazol-4-yl)acetamido]-1-oxadethia-3-cephem-4-carboxylic acid (syn isomer), crystal, mp 132° to 139° C.

(58) 7β-[2-ethoxyimino-2-(2-aminothiazol-4-yl)acetamido]-1-oxadethia-3-cephem-4-carboxylic acid hydrochloride (syn isomer), crystal, mp 150° to 158° C. (dec.).

(59) Benzyl 7β-[2-(2-formamidothiazol-4-yl)acetamido]-1-oxadethia-3-cephem-4-carboxylate.

I.R. (Nujol): 3300, 3110, 1780, 1725, 1695, 1650, 1540 cm⁻¹.

(60) 7β-[2-(2-Formamidothiazol-4-yl)acetamido]-1-oxadethia-3-cephem-4-carboxylic acid.

I.R. (Nujol): 3280, 3100, 1770, 1720, 1695, 1650 cm⁻¹.

(61) 7β-[2-(2-Aminothiazol-4-yl)acetamido]-1-oxadethia-3-cephem-4-carboxylic acid.

I.R. (Nujol): 3540, 3480, 3250, 3050, 1770, 1660 cm⁻¹.

EXAMPLE 3

Benzyl 2-[2-oxo-3β-phenoxyacetamido-4α-(2-phenoxyacetoxyethoxy)azetidin-1-yl]-3-methyl-2-butenoate obtained in Example 1(a)(2) was in turn treated according to similar manners to those of Examples 1(a) (3)(i), 1(a)(4)(i), 1(a)(5), 1(a)(6), 1(a)(7) and 1(b)(1) to 1(b)(3) to give 4-benzyloxycarbonyl-7β-phenoxyacetamido-1-oxa-5-aza-6β-bicyclo[4,2,0]-oct-3-ene-8-one, which has the following structural formula:

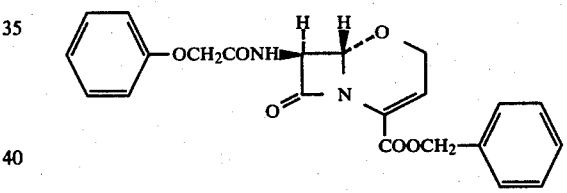

mp 131° to 134° C.

I.R. (Nujol): 3300, 1780, 1715, 1675 cm⁻¹.

N.M.R. (CDCl₃, δ): 4.55 (4H, m), 4.9–5.3 (2H, m), 5.37 (2H, s), 6.43 (1H, t, J=3 Hz), 6.9–7.5 (11H, m).

EXAMPLE 4

Pyridine (194 mg.) and phosphorus pentachloride (510 mg.) were added at −20° to −25° C. to a solution of benzyl 7β-phenoxyacetamido-1-oxadethia-3-cephem-4-carboxylate (690 mg.) in methylene chloride (25 ml.). The resulting mixture was stirred for 30 minutes at −20° to −25° C., for 2 hours under ice-cooling and for 1.5 hours at ambient temperature. To the reaction mixture was added dropwise methanol (520 mg.) at −20° C. and the reaction temperature was elevated to 0° C. over 30 minutes. After stirring for 30 minutes at the same temperature, water (0.5 ml.) was added thereto and the mixture was stirred for 1 hour at 0° C. The reaction mixture was extracted three times with water (3 ml.). The aqueous extracts were combined, adjusted to pH 7 to 8 with sodium bicarbonate and extracted with ethyl acetate (20 ml. and 10 ml.). The extracts were combined, dried over magnesium sulfate and concentrated under reduced pressure to give oil of benzyl 7β-amino-1-oxadethia-3-cephem-4-carboxylate (190 mg.).

I.R. (CHCl$_3$): 3350, 1785, 1720 cm$^{-1}$.
N.M.R. (CDCl$_3$, δ): 4.4–4.6 (3H, m), 5.02 (1H, d, J=4 Hz), 5.25 (2H, s), 6.50 (1H, t, J=2 Hz), 7.45 (5H, s).

EXAMPLE 5

Benzyl 7β-phenoxyacetamido-1-oxadethia-3-cephem-4-carboxylate (408 mg.) was treated according to a similar manner to that of Example 4 and the reaction mixture was extracted with water (10 ml. and 5 ml.). The aqueous extracts were combined, adjusted to pH 7 to 8 with sodium bicarbonate under ice-cooling and then extracted with ethyl acetate (25 ml. and 15 ml.). The extracts were combined, dried over magnesium sulfate and concentrated under reduced pressure to a volume of 5 ml. A solution of p-toluenesulfonic acid (170 mg.) in ethyl acetate (5 ml.) was added dropwise thereto to give precipitates. After stirring for an hour, the precipitates were collected by filtration, washed with a small amount of ethyl acetate and dried under reduced pressure to give benzyl 7β-amino-1-oxadethia-3-cephem-4-carboxylate p-toluenesulfonate (230 mg.), mp 148° to 153° C. (dec.).
I.R. (Nujol): 1795, 1720 cm$^{-1}$.
N.M.R. (d$_6$-DMSO, δ): 2.30 (3H, s), 4.67 (2H, d, J=3 Hz), 5.03 (1H, d, J=4 Hz), 5.30 (1H, d, J=4 Hz), 5.32 (2H, s), 6.70 (1H, t, J=3 Hz), 7.10 (2H, d, J=8 Hz), 7.38 (5H, s), 7.52 (2H, d, J=8 Hz).

EXAMPLE 6

To a solution of 7β-phenoxyacetamido-1-oxadethia-3-cephem-4-carboxylic acid (740 mg.) in methylene chloride (15 ml.) were added successively triethylamine (282 mg.) and trimethylsilyl chloride (380 mg.) with stirring under ice-cooling. The mixture was stirred for 40 minutes at the same temperature and then cooled to −45° C. and to the mixture was added N,N-dimethylaniline (646 mg.) and powdered phosphorus pentachloride (956 mg.). The resulting mixture was stirred for 1.5 hours at −35° to −30° C., cooled to −45° C. and thereto was added methanol (2.1 ml.). The temperature was raised to 0° C. over a period of 70 minutes and water (2.1 ml.) was added thereto and the mixture was stirred for 20 minutes at 0° C. The reaction mixture was adjusted to pH 3 with a saturated aqueous solution of sodium bicarbonate. The precipitates were collected by filtration, washed with methylene chloride and then suspended in water (2 ml.). The suspension was adjusted to pH 3 with 1 N hydrochloric acid and the precipitates were collected by filtration to give 7β-amino-1-oxadethia-3-cephem-4-carboxylic acid (247 mg.). The mother liquor was allowed to stand under cooling and then filtered to give the same compound (8 mg.).
I.R. (Nujol): 2700–2270, 2120, 1805, 1630, 1540, 1505 cm$^{-1}$.
N.M.R. (DCl+D$_2$O, δ) (internal reference: DSS): 4.77 (2H, m), 5.06 (1H, d, J=4 Hz), 5.40 (1H, d, J=4 Hz), 6.81 (1H, t, J=3 Hz).

EXAMPLE 7

The following compound was prepared according to the similar manners to those of Examples 4 to 6.
(1) Benzyl 7α-methoxy-7β-amino-1-oxadethia-3-cephem-4-carboxylate, oil.
I.R. (CH$_2$Cl$_2$): 1785, 1725 cm$^{-1}$.

EXAMPLE 8

A solution of benzyl 7β-amino-1-oxadethia-3-cephem-4-carboxylate (1.12 g.) and 3,5-di(tert-butyl)-4-hydroxybenzaldehyde (1.12 g.) in methylene chloride (40 ml.) was refluxed for 2 hours with dehydrating by using molecular sieves 3A. To the reaction mixture containing benzyl 7β-[3,5-di(tert-butyl)-4-hydroxybenzylidene]amino-1-oxadethia-3-cephem-4-carboxylate was added methylene chloride (30 ml.) followed by cooling at −10° to −15° C., and to the reaction mixture were added magnesium sulfate (4 g.) and nickel peroxide (2.8 g.). The resultant mixture was stirred at −15° to −10° C. for 30 minutes and at room temperature for an additional 10 minutes, and then insoluble substances were filtered off. To the filtrate containing benzyl 7β-[3,5-di(tert-butyl)-4-oxophenylidene]methylamino-1-oxadethia-3-cephem-4-carboxylate was added methanol (40 ml.), and the mixture was stirred for 3 hours at room temperature and the solvent was distilled off. Thus obtained benzyl 7α-methoxy-7β-[3,5-di(tert-butyl)-4-hydroxybenzylidene]amino-1-oxadethia-3-cephem-4-carboxylate was dissolved in a mixture of methanol (40 ml.) and tetrahydrofuran (10 ml.) and then (carboxymethyl)-trimethylammonium chloride hydrazide (1.01 g.) was added thereto. The resultant mixture was stirred for 1.5 hours at room temperature and then concentrated to the volume of about 5 ml. To the residue was added water (20 ml.), and the mixture was extracted with ethyl acetate (50 ml.). The extract was washed with water, dried over magnesium sulfate and then evaporated. The residue was subjected to column chromatography on silica gel (10 g.) and eluted first with methylene chloride and then with a mixture of methylene chloride and ethyl acetate (1:1). The fractions containing the object compound were evaporated to give an oil of benzyl 7α-methoxy-7β-amino-1-oxadethia-3-cephem-4-carboxylate (850 mg.).
I.R. (CH$_2$Cl$_2$): 1785, 1725 cm$^{-1}$.
N.M.R. (CDCl$_3$, δ): 3.50 (3H, s), 4.52 (2H, m), 4.82 (1H, s), 5.30 (2H, s), 6.38 (1H, t, J=3 Hz), 7.36 (5H, s).

EXAMPLE 9

Dimethylformamide (65 mg.) was added to ethyl acetate (1 ml.), and phosphorus oxychloride (137 mg.) was added dropwise thereto under ice-cooling and stirring. After stirring for 1 hour under ice-cooling, 2-methoxyimino-2-(2-formamidothiazol-4-yl)acetic acid (syn isomer) (170 mg.) was at a time added thereto, and the mixture was stirred for 1 hour at the same temperature. On the other hand, benzyl 7β-amino-1-oxadethia-3-cephem-4-carboxylate (150 mg.) was dissolved in a mixture of ethyl acetate (7 ml.) and bis(trimethylsilyl)acetamide (370 mg.). To this solution was at a time added at −30° C. the ethyl acetate solution obtained above. The resulting mixture was stirred for 1 hour at −20° to −25° C. and for 1 hour at 0° to 5° C. Ethyl acetate (10 ml.) was added to the reaction mixture, and the resulting mixture was in turn washed with 5% hydrochloric acid (10 ml.), water (10 ml.), 5% soldium bicarbonate aqueous solution (10 ml.) and water (10 ml.×2). The ethyl acetate layer was dried over magnesium sulfate and concentrated under reduced pressure to give oil (240 mg.). The oil was pulverized with diethyl ether (20 ml.), and the powder was collected by filtration, washed with diethyl ether and dried to give powder of benzyl 7β-[2-methoxyimino-2-(2-formamidothiazol-4-yl)acetamido]-1-oxadethia-3-cephem-4-carboxylate (syn isomer) (95 mg.).
I.R. (Nujol): 3250, 1795, 1725, 1690, 1680 cm$^{-1}$.
N.M.R. (CDCl$_3$, δ): 3.96 (3H, s), 4.50 (2H, broad s), 5.12 (1H, d, J=4 Hz), 5.24 (2H, s), 5.78 (1H, dd, J=4, 8

Hz), 6.48 (1H, t, J=2 Hz), 7.23 (1H, s), 7.34 (5H, s), 7.56 (1H, d, J=8 Hz), 9.56 (1H, s).

EXAMPLE 10

To a mixture of N,N-dimethylformamide (0.591 g.) in ethyl acetate (6 ml.) was added a mixture of phosphorus oxychloride (0.620 g.) in ethyl acetate (3 ml.) under ice-cooling followed by stirring under ice-cooling. To the resultant solution was added 2-ethoxyimino-2-(2-formamidothiazol-4-yl)acetic acid (syn isomer) (945 mg.) under stirring and then stirring was continued under ice-cooling for an hour to give a homogeneous solution. On the other hand, benzyl 7β-amino-1-oxadethia-3-cephem-4-carboxylate p-toluenesulfonate (1.45 g.) was added to a mixture of an aqueous solution of sodium bicarbonate and ethyl acetate and then the ethyl acetate layer was separated. The remaining aqueous layer was extracted twice with ethyl acetate. The combined ethyl acetate layers were dried over magnesium sulfate, and evaporated. The resulting residue was dissolved in ethyl acetate (25 ml.) and cooled to −50° C. To the solution were successively added at −50° C. pyridine (0.65 ml.) and the homogenous solution obtained above at a time. To the reaction mixture was added ethyl acetate (10 ml.) and the mixture was stirred for 1.5 hours. To the resulting mixture was added water followed by stirring at 0° C. The ethyl acetate layer was separated and the remaining aqueous layer was extracted with ethyl acetate. The combined ethyl acetate layers were washed successively with 1 N hydrochloric acid, a saturated aqueous solution of sodium bicarbonate and an aqueous solution of sodium chloride, and dried over magnesium sulfate and then evaporated. The residue was pulverized in diethyl ether, collected by filtration and then dried to give benzyl 7β-[2-ethoxyimino-2-(2-formamidothiazol-4-yl)acetamido]-1-oxadethia-3-cephem-4-carboxylate (syn isomer) (1.55 g.), mp 120° C.

I.R. (Nujol): 1785, 1720, 1680 cm$^{-1}$.

N.M.R. (d$_6$-DMSO, δ): 1.22 (3H, t), 4.12 (2H, q), 4.54 (2H, m), 5.12 (1H, d, J=4 Hz), 5.28 (2H, s), 5.66 (1H, dd, J=4, 9 Hz), 6.60 (1H, m), 7.40 (6H, s), 8.50 (1H, s), 9.38 (1H, d, J=9 Hz), 12.60 (1H, s)

EXAMPLE 11

To a solution of N,N-dimethylformamide (0.540 g.) in ethyl acetate (10 ml.) was added a solution of phosphorus oxychloride (0.610 g.) in ethyl acetate (3 ml.) under ice-cooling followed by stirring under ice-cooling for 1 hour and 20 minutes. To the mixture was added 2-isopropoxyimino-2-(2-formamidothiazol-4-yl)acetic acid (syn isomer) (950 mg.) and the resulting homogenous solution was stirred for 1 hour and 10 minutes at the same temperature and then cooled to −20° C. On the other hand, benzyl 7β-amino-1-oxadethia-3-cephem-4-carboxylate p-toluenesulfonate (1.27 g.) was added to a mixture of ethyl acetate and a saturated aqueous solution of sodium bicarbonate and the ethyl acetate layer was separated. The remaining aqueous layer was extracted twice with ethyl acetate. The combined ethyl acetate layers were washed with an aqueous solution of sodium chloride, dried over magnesium sulfate and then concentrated. Thus obtained benzyl 7β-amino-1-oxadethia-3-cephem-4-carboxylate was dissolved in ethyl acetate (20 ml.) and cooled to −50° C. To the solution were successively added at −50° C. pyridine (0.584 g.) and the homogenous solution obtained above in one portion. To the mixture was added ethyl acetate (10 ml.), and then the temperature of the reaction mixture was gradually raised to −20° C. in 75 minutes and subsequently to −10° C. in 110 minutes. After addition of water, the ethyl acetate layer was separated from the mixture. The remaining aqueous layer was extracted with ethyl acetate. The combined ethyl acetate layers were washed successively with 1 N hydrochloric acid, a saturated aqueous solution of sodium bicarbonate and an aqueous solution of sodium chloride, dried over magnesium sulfate and then concentrated. The residue was crystallized in a mixture of ethyl acetate and diethyl ether to give crystals of benzyl 7β-[2-isopropoxyimino-2-(2-formamidothiazol-4-yl)acetamido]-1-oxadethia-3-cephem-4-carboxylate (syn isomer) (1.16 g.), mp 162° to 166° C. Further, the same object compound was obtained from the mother liquor (0.185 g.).

I.R. (Nujol): 3290, 3150, 1790, 1710, 1690, 1640 cm$^{-1}$.

N.M.R. (d$_6$-DMSO, δ): 1.25 (6H, d, J=6 Hz), 4.38 (1H, m), 4.60 (2H, d, J=3 Hz), 5.24 (1H, d, J=4 Hz), 5.70 (1H, dd, J=4,8 Hz), 5.31 (2H, s), 6.65 (1H, t, J=3 Hz), 7.43 (6H, s), 8.56 (1H, s), 9.35 (1H, d, J=8 Hz), 12.70 (1H, s).

EXAMPLE 12

To a solution of phosphorus oxychloride (0.411 g.) in methylene chloride (5 ml.) was added N,N-dimethylformamide (3.5 ml.) under ice-cooling followed by stirring for 40 minutes at room temperature. The resulting mixture was cooled to −25° C. and thereto was added 2-methoxyimino-2-(6-formamidopyridin-2-yl)acetic acid (syn isomer) (0.6 g.) followed by stirring for 50 minutes at about −20° C. On the other hand, benzyl 7β-amino-1-oxadethia-3-cephem-4-carboxylate p-toluenesulfonate (1.0 g.) was added to a mixture of a saturated aqueous solution of sodium bicarbonate and ethyl acetate and then the ethyl acetate layer was separated. The remaining aqueous layer was extracted with ethyl acetate. The combined ethyl acetate layers were dried over magnesium sulfate and then concentrated. The obtained oily substance (636 mg.) was dissolved in methylene chloride (25 ml.) and cooled at −50° C., and thereto were successively added pyridine (0.44 ml.) and the cooled mixture obtained above at a time. The temperature was gradually raised to −10° C. over a period of an hour. The reaction mixture was poured into a cooled mixture of ethyl acetate (150 ml.) and an aqueous solution of sodium bicarbonate. The ethyl acetate layer was separated and the remaining aqueous solution was extracted with ethyl acetate. The combined ethyl acetate layers were washed successively with an aqueous solution of sodium bicarbonate, 1 N-hydrochloric acid and an aqueous solution of sodium chloride, dried over magnesium sulfate and then concentrated. The residue was crystallized, which was washed with diethyl ether and dried to give benzyl 7β-[2-methoxyimino-2-(6-formamidopyridin-2-yl)acetamido]-1-oxadethia-3-cephem-4-carboxylate (syn isomer) (819 mg.), which was decomposed up to 170° C.

I.R. (Nujol): 3280, 1810, 1720, 1615 cm$^{-1}$.

N.M.R. (d$_6$-DMSO, δ): 4.60 (2H, d, J=3 Hz), 6.63 (1H, t, J=3 Hz), 5.23 (1H, d, J=4 Hz), 5.75 (1H, dd, J=4,9 Hz), 9.33 (1H, d, J=9 Hz), 3.99 (3H, s), 5.30 (2H, s), 9.38 (1H, d, J=8 Hz), 10.60 (1H, d, J=8 Hz).

EXAMPLE 13

Benzyl 7β-amino-1-oxadethia-3-cephem-4-carboxylate p-toluenesulfonate (1.50 g.) was added to a cooled mixture of ethyl acetate and a saturated aqueous solution of sodium bicarbonate. The ethyl acetate layer was separated and the remaining aqueous layer was extracted with ethyl acetate. The combined ethyl acetate layers were washed with an aqueous solution of sodium chloride dried over magnesium sulfate and then evaporated. The residue was dissolved in methylene chloride (25 ml.) and thereto was added D,L-2-sulfo-2-phenylacetic acid anhydride with monoethyl carbonate (triethylamine salt, 1.36 g.) under ice-cooling followed by stirring at the same temperature for an hour. To the mixture was further added D,L-2-sulfo-2-phenylacetic acid anhydride with mono-ethyl carbonate (triethylamine salt 90 mg.) and then stirred for 15 minutes. To the reaction mixture was added methylene chloride (100 ml.) and the resulting mixture was washed successively with diluted hydrochloric acid (twice) and an aqueous solution of sodium chloride. The combined washings were extracted with ethyl acetate and the extract was washed with an aqueous solution of sodium chloride. The organic layers were combined and dried over magnesium sulfate and then evaporated to dryness to give an amorphous solid of benzyl 7β-[D,L-2-sulfo-2-phenylacetamido]-1-oxadethia-3-cephem-4-carboxylate (1.6 g.).

I.R. ($CH_2Cl_2$): 3280, 1790, 1720, 1670, 1635 cm$^{-1}$.

N.M.R. (DMSO-$d_6$, δ): 4.5–4.57 (3H, m), 5.15, 5.17 (1H, two d, j=4 Hz), 5.27 (2H, s), 5.63 (1H, d,d, J=4,9 Hz), 6.63 (1H, m), 7.17–7.56 (10H, m), 8.94, 9.00 (1H, two d, J=9 Hz).

EXAMPLE 14

To a suspension of 2-methoxyimino-2-(4-aminopyrimidin-2-yl)acetic acid dihydrate (syn isomer) (600 mg.) in methylene chloride (10 ml.) was added phosphorus oxychloride (0.95 ml.) under ice-cooling and the mixture was stirred for 30 minutes. After addition of N,N-dimethylformamide (1.86 ml.), the resulting mixture was stirred for 40 minutes under cooling and then cooled to −50° C. (Solution A). On the other hand, to a solution of bis(trimethylsilyl)acetamide (2.62 g.) in methylene chloride (10 ml.) was added benzyl 7β-amino-1-oxadethia-3-cephem-4-carboxylate p-toluenesulfonate (1.07 g.) under ice-cooling and the mixture was stirred for 20 minutes. Thus obtained solution was added to the Solution A prepared above and then the temperature was raised to 0° C. over a period of 90 minutes. The reaction mixture was poured into a mixture of ethyl acetate and a cold aqueous solution of sodium bicarbonate. The organic layer was separated and the aqueous layer was further extracted with ethyl acetate. The organic layer and the ethyl acetate extract were combined, washed with an aqueous solution of sodium chloride, dried over magnesium sulfate and then evaporated. To the residue was added diethyl ether and the precipitates were collected by filtration. Thus obtained product was subjected to column chromatography on silica gel (13.5 g.), eluted with ethyl acetate. The fractions containing the desired compound were collected and then evaporated to give benzyl 7β-[2-methoxyimino-2-(4-aminopyrimidin-2-yl)acetamido]-1-oxadethia-3-cephem4-carboxylate (syn isomer) (661 mg.), mp 120° to 137° C.

I.R. (Nujol): 3400, 3300, 1780, 1720, 1670, 1630 cm$^{-1}$.

N.M.R. (DMSO-$d_6$, δ): 3.94 (3H, s), 4.55 (2H, d, J=2 Hz), 5.20 (1H, d, J=4 Hz), 5.30 (2H, s), 5.74 (1H, d,d, J=4 and 9 Hz), 6.40 (1H, d, J=6 Hz), 6.62 (1H, t, J=2 Hz), 7.00 (2H, broad s), 7.41 (5H, s), 8.10 (1H, d, J=6 Hz), 9.12 (1H, d, J=9 Hz)

EXAMPLE 15

To a suspension of 2-methoxyimino-2-(5-amino-1,2,4-thiadiazol-3-yl)acetic acid (syn isomer) (600 mg.) in methylene chloride (10 ml.) was added phosphorus oxychloride (0.545 ml.) at room temperature and the mixture was stirred for an hour. After addition of N,N-dimethylformamide (1.13 g.) at −22° C., the resulting mixture was stirred for 70 minutes at −15° to −7° C. and then cooled to −25° C. (Solution A.). On the other hand, benzyl 7β-amino-1-oxadethia-3-cephem-4-carboxylate p-toluenesulfonate (1.12 g.) was added to a solution of bis(trimethylsilyl)acetamide (2.82 g.) in methylene chloride (10 ml.) under ice cooling and the mixture was stirred for 30 minutes. The resulting solution was cooled to −25° C. and added to the Solution A prepared above, and then the temperature was raised to −3° C. over a period of 70 minutes. The reaction mixture was poured into a mixture of ethyl acetate and a cold aqueous solution of sodium bicarbonate. The organic layer was separated therefrom, washed with an aqueous solution of sodium chloride, dried over magnesium sulfate and then evaporated. The residue was subjected to column chromatography on silica gel (15 g.), eluted with a mixture of benzene and ethyl acetate (1:4). The fractions containing the desired compound were collected and evaporated to give benzyl 7β-[2-methoxyimino-2-(5-amino-1,2,4-thiadiazol-3-yl)acetamido]-1-oxadethia-3-cephem-4-carboxylate (syn isomer) (1.03 g.).

I.R. (Nujol): 3450, 3360, 3240, 1790, 1735, 1675 cm$^{-1}$.

N.M.R. (DMSO-$d_6$, δ): 3.92 (3H, s), 4.55 (2H, d, J=2 Hz), 5.19 (1H, d, J=4 Hz), 5.30 (2H, s), 5.70 (1H, dd, J=4 and 9 Hz), 6.61 (1H, t, J=2 Hz), 7.40 (5H, s), 8.10 (2H, broad s), 9.28 (1H, d, J=9 Hz).

EXAMPLE 16

The following compounds were prepared according to the similar manners to those of Examples 9 to 15.

(1) Benzyl 7β-[2-n-butoxyimino-2-(2-formamidothiazol-4-yl)acetamido]-1-oxadethia-3-cephem-4-carboxylate (syn isomer).

I.R. (Nujol): 1780, 1720, 1670, 1630 cm$^{-1}$.

N.M.R. ($d_6$-DMSO, δ): 0.90 (3H, t, J=6 Hz), 1.0–1.9 (4H, m), 4.10 (2H, d, J=3 Hz), 4.57 (2H, m), 5.20 (1H, d, J=4 Hz), 5.29 (2H, s), 5.67 (1H, dd, J=4,8 Hz), 6.61 (1H, t, J=3 Hz), 7.40 (6H, s), 8.55 (1H, s), 9.38 (1H, d, J=8 Hz), 12.70 (1H, s).

(2) Benzyl 7β-[2-n-pentyloxyimino-2-(2-formamidothiazol-4-yl)acetamido]-1-oxadethia-3-cephem-4-carboxylate (syn isomer), mp 136° to 147° C.

I.R. (Nujol): 1780, 1725, 1690, 1670, 1630 cm$^{-1}$.

N.M.R. ($d_6$-DMSO, δ): 0.88 (3H, t, J=6 Hz), 1.0–1.7 (6H, m), 4.07 (2H, t), 4.54 (2H, d, J=3 Hz), 5.16 (1H, d, J=4 Hz), 5.25 (2H, s), 5.63 (1H, dd, J=4,8 Hz), 6.59 (1H, t, J=3 Hz), 7.36 (6H, s), 8.50 (1H, s), 9.34 (1H, d, J=8 Hz).

(3) Benzyl 7β-(2-methoxyimino-2-phenylacetamido)-1-oxadethia-3-cephem-4-carboxylate (syn isomer), mp 157° to 158.5° C.

I.R. (Nujol): 3280, 1770, 1730, 1660, 1630 cm$^{-1}$.

N.M.R. ($d_6$-DMOS, δ): 3.92 (3H, s), 4.59 (2H, d, J=3 Hz), 5.24 (1H, d, J=4 Hz), 5.30 (2H, s), 5.70 (1H, dd, J=4,8 Hz), 6.61 (1H, t, J=3 Hz), 7.4–7.65 (10H, m), 9.49 (1H, d, J=8 Hz).

(4) Benzyl 7β-[2-(2-formamidothiazol-4-yl)glyoxylamido]-1-oxadethia-3-cephem-4-carboxylate, mp 220° to 221° C. (dec.).

I.R. (Nujol): 3150, 1780, 1725, 1695, 1670 cm$^{-1}$.

N.M.R. (d$_6$-DMSO, δ): 4.60 (2H, d, J=3 Hz), 5.25 (1H, d, J=4 Hz), 5.70 (1H, dd, J=4,8 Hz), 5.33 (2H, s), 6.66 (1H, t, J=3 Hz), 7.45 (5H, s), 8.48 (1H, s), 8.61 (1H, s), 9.60 (1H, d, J=8 Hz), 12.50 (1H, broad s).

(5) Benzyl 7β-[2-methoxyimino-2-(5,6-dihydro-1,4-oxathiin-2-yl)acetamido]-1-oxadethia-3-cephem-4-carboxylate (syn isomer).

I.R. (Nujol): 3400, 1795, 1725, 1680, 1640 cm$^{-1}$.

N.M.R. (CDCl$_3$, δ): 3.05 (2H, m), 4.00 (3H, s), 4.43 (2H, m), 4.57 (2H, d, J=3 Hz), 5.14 (1H, d, J=4 Hz), 5.31 (2H, s), 5.71 (1H, dd, J=4,9 Hz), 5.95 (1H, s), 6.54 (1H, t, J=3 Hz), 6.54 (1H, d, J=9 Hz), 7.42 (5H, s).

(6) Benzyl 7β-[2-(1H-1,2,3,4-tetrazol-1-yl)acetamido]-1-oxadethia-3-cephem-4-carboxylate, mp 181° to 183° C.

I.R. (Nujol): 3280, 1790, 1725, 1690, 1675 cm$^{-1}$.

N.M.R. (d$_6$-DMSO, δ): 4.62 (2H, d, J=3 Hz), 5.25 (1H, d, J=4 Hz), 5.33 (2H, s), 5.40 (2H, s), 5.65 (1H, dd, J=4,8 Hz), 6.70 (1H, t, J=3 Hz), 7.43 (5H, s), 9.33 (1H, d, J=8 Hz), 9.38 (1H, s).

(7) Benzyl 7β-[2-methoxyimino-2-(2-furyl)acetamido]-1-oxadethia-3-cephem-4-carboxylate (syn isomer).

I.R. (Nujol): 3390, 1795, 1730, 1690, 1635 cm$^{-1}$.

N.M.R. (d$_6$-DMSO, δ): 3.90 (3H, s), 4.56 (2H, d, J=3 Hz), 5.22 (1H, d, J=4 Hz), 5.30 (2H, s), 5.65 (1H, dd, J=4,8 Hz), 6.62 (3H, m), 7.83 (1H, m), 7.44 (5H, s), 9.54 (1H, d, J=8 Hz).

(8) 7β-[2-Ethoxyimino-2-(2-aminothiazol-4-yl)acetamido]-1-oxadethia-3-cephem-4-carboxylic acid (syn isomer), which is gradually decomposed from 150° C.

(9) 7β-[2-Isopropoxyimino-2-(2-formamidothiazol-4-yl)acetamido]-1-oxadethia-3-cephem-4-carboxylic acid (syn isomer), mp 171° to 210° C. (dec.).

(10) 7β-[2-Isopropoxyimino-2-(2-aminothiazol-4-yl)acetamido]-1-oxadethia-3-cephem-4-carboxylic acid hydrochloride (syn isomer), which is softened at 65° to 70° C. and gradually decomposed up to 140° C.

(11) 7β-[2-n-Butoxyimino-2-(2-formamidothiazol-4-yl)acetamido]-1-oxadethia-3-cephem-4-carboxylic acid (syn isomer), which is decomposed up to 165° C.

(12) 7β-[2-n-Butoxyimino-2-(2-aminothiazol-4-yl)acetamido]-1-oxadethia-3-cephem-4-carboxylic acid (syn isomer), dp>200° C.

(13) 7β-[2-n-Pentyloxyimino-2-(2-formamidothiazol-4-yl)acetamido]-1-oxadethia-3-cephem-4-carboxylic acid (syn isomer), mp 142° to 147° C. (dec.).

(14) 7β-[2-n-Pentyloxyimino-2-(2-aminothiazol-4-yl)acetamido]-1-oxadethia-3-cephem-4-carboxylic acid hydrochloride (syn isomer) (powder), mp 118° to 124° C. (dec.).

(15) 7β-[2-Methoxyimino-2-(6-formamidopyridin-2-yl)acetamido]-1-oxadethia-3-cephem-4-carboxylic acid (syn isomer), mp 130° to 160° C. (dec.).

(16) 7β-[2-Methoxyimino-2-(6-aminopyridin-2-yl)acetamido]-1-oxadethia-3-cephem-4-carboxylic acid hydrochloride (syn isomer) (powder), mp 100° to 140° C. (dec.).

(17) 7β-(2-Methoxyimino-2-phenylacetamido)-1-oxadethia-3-cephem-4-carboxylic acid (syn isomer), mp 80° to 95° C. (dec.).

(18) 7β-[2-(2-Formamidothiazol-4-yl)glyoxylamido]-1-oxadethia-3-cephem-4-carboxylic acid, mp 200° to 220° C. (dec.).

(19) 7β-[2-(2-Aminothiazol-4-yl)glyoxylamido]-1-oxadethia-3-cephem-4-carboxylic acid, dp>240° C.

(20) 7β-[2-(1H-1,2,3,4-Tetrazol-1-yl)acetamido]-1-oxadethia-3-cephem-4-carboxylic acid, mp 164° to 167° C. (dec.).

(21) 7β-[2-Methoxyimino-2-(2-furyl)acetamido]-1-oxadethia-3-cephem-4-carboxylic acid (syn isomer), mp 197° C. (dec.).

(22) 7β-[2-Methoxyimino-2-(5,6-dihydro-1,4-oxathiin-2-yl)acetamido]-1-oxadethia-3-cephem-4-carboxylic acid (anti isomer), mp 163° to 165° C. (dec.).

(23) 7β-(D,L-2-sulfo-2-phenylacetamido)-1-oxadethia 3-cephem-4-carboxylic acid (amorphous solid).

I.R. (KBr): 1790, 1730, 1680 cm$^{-1}$.

(24) Benzyl 7β-phenoxyacetamido-1-oxadethia-3-cephem-4-carboxylate, powder.

I.R. (CHCl$_3$): 3420, 1795, 1725, 1690 cm$^{-1}$.

(25) 4-Benzyloxycarbonyl-7β-phenoxyacetamido-1-oxa-5-aza-6β-bicyclo[4,2,0]oct-3-ene-8-one, mp 131° to 134° C.

(26) 7β-Phenoxyacetamido-1-oxadethia-3-cephem-4-carboxylic acid, mp 174° to 176° C.

(27) 7β-[2-Methoxyimino-2-(2-formamidothiazol-4-yl)acetamido]-1-oxadethia-3-cephem-4-carboxylic acid (syn isomer).

I.R. (Nujol): 3600-2200, 1780, 1720, 1670 cm$^{-1}$.

(28) 7β-[2-Methoxyimino-2-(2-aminothiazol-4-yl)acetamido]-1-oxadethia-3-cephem-4-carboxylic acid hydrochloride (syn isomer).

I.R. (Nujol): 3400-2400, 1780, 1730, 1680, 1640 cm$^{-1}$.

(29) 7β-[2-Methoxyimino-2-(2-aminothiazol-4-yl)acetamido]-1-oxadethia-3-cephem-4-carboxylic acid (syn isomer), powder.

I.R. (Nujol): 3600-2400, 1785, 1720, 1660 cm$^{-1}$.

(30) Benzyl 7β-[2-allyloxyimino-2-(2-formamidothiazol-4-yl)acetamido]-1-oxadethia-3-cephem-4-carboxylate (syn isomer), amorphous solid.

I.R. (CH$_2$Cl$_2$): 3370, 3250-3020, 1790, 1720, 1680, 1630 cm$^{-1}$.

N.M.R. (DMSO-d$_6$, δ): 4.6 (4H, m), $$5.12 - 5.44 \left\{5H \left\{ \begin{array}{l} 5.22 \text{ (d, j = 4Hz)} \\ 5.29 \text{ (s)} \end{array} \right. \right\}$$

5.67 (1H, dd, J=4 and 8 Hz), 5.76–6.16 (1H, m), 6.61 (1H, m), 7.42 (5H+1H, s), 8.53 (1H, s), 9.49 (1H, d, J=8 Hz), 12.63 (1H, s).

(31) Benzyl 7β-[2-{2-propynyloxyimino}-2-(2-formamidothiazol-4-yl)acetamido]-1-oxadethia-3-cephem-4-carboxylate (syn isomer).

I.R. (CH$_2$Cl$_2$): 3380, 3290, 1790, 1720, 1680, 1635, 1540 cm$^{-1}$.

N.M.R. (DMSO-d$_6$, δ): 3.67 (1H, t, J=2 Hz), 4.59 (2H, m), 4.78 (2H, d, J=2 Hz), 5.25 (1H, d, J=4 Hz), 5.30 (2H, s), 5.70 (1H, dd, J=4 and 8 Hz), 6.66 (1H, s), 7.47 (5H+1H, s), 8.61 (1H, s), 9.57 (1H, d, J=8 Hz).

(32) Benzyl 7β-[2-benzyloxyimino-2-(2-formamidothiazol-4-yl)acetamido]-1-oxadethia-3-cephem-4-carboxylate (syn isomer).

I.R. (CH$_2$Cl$_2$): 3350, 3270-3120, 1790, 1720, 1680, 1630, 1540 cm$^{-1}$.

N.M.R. (DMSO-d$_6$, δ): 4.56 (2H, m), 5.20 (2H, s), 5.28 (2H, s), 5.22 (1H, d, J=4 Hz), 5.70 (1H, dd, J=4 and 8 Hz), 6.62 (1H, m), 7.4 (11H, s), 8.52 (1H, s), 9.55 (1H, d, J=8 Hz), 12.56 (1H, s).

(33) 7β-[2-Methoxyimino-2-(4-aminopyrimidin-2-yl)acetamido]-1-oxadethia-3-cephem-4-carboxylic acid (syn isomer), crystal.

I.R. (Nujol): 3460, 3350, 3260, 1780, 1630 cm$^{-1}$.

(34) 7β-[2-Methoxyimino-2-(5-amino-1,2,4-thiadiazol-3-yl)acetamido]-1-oxadethia-3-cephem-4-carboxylic acid (syn isomer), powder.
I.R. (Nujol): 3400, 3350, 3260, 1780, 1700, 1640 cm$^{-1}$.

(35) 7β-[2-Allyloxyimino-2-(2-formamidothiazol-4-yl)acetamido]-1-oxadethia-3-cephem-4-carboxylic acid (syn isomer).
I.R. (Nujol): 3450, 3330, 3170, 1770, 1690, 1645, 1635, 1620, 1540 cm$^{-1}$.

(36) 7β-[2-(2-Propynyloxyimino)-2-(2-formamidothiazol-4-yl)acetamido]-1-oxadethia-3-cephem-4-carboxylic acid (syn isomer).
I.R. (Nujol): 3250, 1780, 1720, 1680, 1660 cm$^{-1}$.

(37) 7β-[2-Benzyloxyimino-2-(2-formamidothiazol-4-yl)acetamido]-1-oxadethia-3-cephem-4-carboxylic acid (syn isomer), crystalline solid.
I.R. (Nujol): 3250, 1780, 1670, 1540 cm$^{-1}$.

(38) 7β-[2-Allyloxyimino-2-(2-aminothiazol-4-yl)acetamido]-1-oxadethia-3-cephem-4-carboxylic acid (syn isomer).
I.R. (Nujol): 3300, 1780, 1660, 1540 cm$^{-1}$.

(39) 7β-[2-(2-Propynyloxyimino)-2-(2-aminothiazol-4-yl)acetamido]-1-oxadethia-3-cephem-4-carboxylic acid hydrochloride (syn isomer), which is gradually decomposed with coloration till 160° C.

(40) 7β-[2-Benzyloxyimino-2-(2-aminothiazol-4-yl)acetamido]-1-oxadethia-3-cephem-4-carboxylic acid (syn isomer), mp. 150° to 170° C. (gradually decomposed with coloration).

(41) Benzyl 7β-[2-methoxyimino-2-(5,6-dihydro-1,4-oxathiin-2-yl)acetamido]-1-oxadethia-3-cephem-4-carboxylate (anti isomer), mp 142° to 144° C.

(42) Benzyl 7α-methoxy-7β-[2-methoxyimino-2-(2-formamidothiazol-4-yl)acetamido]-1-oxadethia-3-cephem-4-carboxylate (syn isomer), amorphous solid.
I.R. (CH$_2$Cl$_2$): 3350, 1780, 1720, 1690 cm$^{-1}$.
N.M.R. (CDCl$_3$, δ): 3.68 (3H, s), 3.96 (3H, s), 4.58 (2H, d, J=2 Hz), 5.20 (1H, s), 5.35 (2H, s), 6.53 (1H, t, J=2 Hz), 7.43 (5H, s), 7.50 (1H, s), 8.70 (1H, s).

(43) Benzyl 7α-methoxy-7β-[2-(2-formamidothiazol-4-yl)acetamido]-1-oxadethia-3-cephem-4-carboxylate.
I.R. (CH$_2$Cl$_2$): 3350, 1780, 1720, 1690 cm$^{-1}$.
N.M.R. (DMSO-d$_6$, δ): 3.44 (3H, s), 3.65 (2H, s), 4.54 (2H, d, J=3 Hz), 5.14 (1H, s), 5.35 (2H, s), 6.62 (1H, t, J=3 Hz), 7.03 (1H, s), 7.50 (5H, s), 7.45 (1H, s), 8.55 (1H, s), 12.38 (1H, broad s).

(44) 7α-Methoxy-7β-[2-methoxyimino-2-(2-formamidothiazol-4-yl)acetamido]-1-oxadethia-3-cephem-4-carboxylic acid (syn isomer), amorphous solid.
N.M.R. (Acetone-d$_6$, δ): 3.58 (3H, s), 3.97 (3H, s), 4.68 (2H, m), 5.16 (1H, s), 6.40 (1H, t, J=3 Hz), 7.60 (1H, s), 8.70 (1H, s), 8.75 (1H, s).

(45) 7α-Methoxy-7β-[2-(2-formamidothiazol-4-yl)acetamido]-1-oxadethia-3-cephem-4-carboxylic acid, amorphous solid.
I.R. (Nujol): 3290, 3150, 1765, 1680 cm$^{-1}$.

(46) 7α-Methoxy-7β-[2-methoxyimino-2-(2-aminothiazol-4-yl)acetamido]-1-oxadethia-3-cephem-4-carboxylic acid hydrochloride (syn isomer).
I.R. (Nujol): 1780, 1720, 1680, 1630 cm$^{-1}$.

(47) 7α-Methoxy-7β[2-(2-aminothiazol-4-yl)acetamido]-1-oxadethia-3-cephem-4-carboxylic acid hydrochloride, powder.
I.R. (KBr): 1780, 1700, 1630 cm$^{-1}$.

(48) 7β-[2-Ethoxyimino-2-(2-formamidothiazol-4-yl)acetamido]-1-oxadethia-3-cephem-4-carboxylic acid (syn isomer), crystal, mp 132° to 139° C.

(49) 7β-[2-Ethoxyimino-2-(2-aminothiazol-4-yl)acetamido]-1-oxadethia-3-cephem-4-carboxylic acid hydrochloride (syn isomer), crystal, mp 150° to 158° C. (dec.).

(50) Benzyl 7β-[2-(2-formamidothiazol-4-yl)acetamido]-1-oxadethia-3-cephem-4-carboxylate.
I.R. (Nujol): 3300, 3110, 1780, 1725, 1695, 1650, 1540 cm$^{-1}$.
N.M.R. (DMSO-d$_6$): 3.64 (2H, s), 4.57 (2H, d, J=3 Hz), 5.17 (1H, d, J=4 Hz), 5.29 (2H, s), 5.60 (1H, dd, J=4 and 8 Hz), 6.65 (1H, t, J=3 Hz), 6.96 (1H, s), 7.38 (5H, s), 8.47 (1H, s), 8.80 (1H, d, J=8 Hz).

(51) 7β-[2-(2-Formamidothiazol-4-yl)acetamido]-1-oxadethia-3-cephem-4-carboxylic acid.
I.R. (Nujol): 3280, 3100, 1770, 1720, 1695, 1650 cm$^{-1}$.

(52) 7β-[2-(2-Aminothiazol-4-yl)acetamido]-1-oxadethia-3-cephem-4-carboxylic acid.
I.R. (Nujol): 3540, 3480, 3250, 3050, 1770, 1660 cm$^{-1}$.

EXAMPLE 17

Anisole (950 mg.) was added to a solution of benzyl 7β-phenoxyacetamido-1-oxadethia-3-cephem-4-carboxylate (370 mg.) in methylene chloride (20 ml.). A solution of aluminum chloride (580 mg.) in nitromethane (5 ml.) was added dropwise thereto under ice-cooling, and the resulting mixture was stirred for 30 minutes under ice-cooling and for 1 hour and 45 minutes at ambient temperature. Ethyl acetate (100 ml.) was added to the reaction mixture, and the mixture was washed with cold 5% hydrochloric acid (20 ml.) and then extracted with 5% aqueous solution of sodium bicarbonate (20 ml. and 10 ml.). The extracts were acidified with 10% hydrochloric acid and then extracted with ethyl acetate (50 ml.). The extract was washed with water, dried and concentrated under reduced pressure. The residue was crystallized with a small amount of ethyl acetate. The crystals were collected by filtration and washed with diethyl ether to give 7β-phenoxyacetamido-1-oxadethia-3-cephem-4-carboxylic acid (190 mg.), mp 174° to 176° C.
I.R. (Nujol): 3400, 3200-2400, 1800, 1740, 1660 cm$^{-1}$.
N.M.R. (d$_6$-DMSO, δ): 4.5-4.6 (4H, m), 5.12 (1H, d, J=4 Hz), 5.56 (1H, dd, J=4, 8 Hz), 6.45 (1H, t, J=2 Hz), 6.8-7.4 (5H, m), 8.75 (1H, d, J=8 Hz).

EXAMPLE 18

Anisole (220 mg.) was added to a solution of benzyl 7β-[2-methoxyimino-2-(2-formamidothiazol-4-yl)acetamido]-1-oxadethia-3-cephem-4-carboxylate (syn isomer) (97 mg.) in dry methylene chloride (10 ml.), and then a solution of aluminum chloride (133 mg.) in nitromethane (2 ml.) was added dropwise thereto under ice-cooling and stirring. The resulting mixture was stirred for 15 minutes under ice-cooling and for 1.5 hours at ambient temperature. The reaction mixture was diluted with ethyl acetate (40 ml.), washed twice with 2% hydrochloric acid (10 ml.) and then extracted with 5% aqueous solution of sodium bicarbonate (15 ml. and 10 ml.). To the extracts was added ethyl acetate (30 ml.) and the mixture was adjusted to pH 1 with 5% hydrochloric acid. The ethyl acetate layer was separated and then the remaining aqueous layer was further extracted twice with ethyl acetate (20 ml.). The ethyl acetate extracts were combined together, dried over magnesium sulfate and concentrated under reduced pressure to give powder of 7β-[2-methoxyimino-2-(2-formamidothiazol-4-yl)acetamido]-1-oxadethia-3-cephem-4-carboxylic acid (syn isomer) (24 mg.).

I.R. (Nujol): 3600–2200, 1780, 1720, 1670 cm$^{-1}$.

N.M.R. (d$_6$-DMSO, δ): 3.90 (3H, s), 4.57 (2H, broad s), 5.20 (1H, d, J=4 Hz), 5.63 (1H, dd, J=4, 8 Hz), 6.33 (1H, t, J=2 Hz), 7.40 (1H, s), 8.53 (1H, s), 9.42 (1H, s), 12.66 (1H, broad s).

EXAMPLE 19

To a solution of benzyl 7β-[2-isopropoxyimino-2-(2-formamidothiazol-4-yl)acetamido]-1-oxadethia-3-cephem-4-carboxylate (syn isomer) (1.22 g.) in methylene chloride (25 ml.) was added anisole (3.84 g.), and thereto was added dropwise a solution of aluminum chloride (1.58 g.) in nitromethane (10 ml.) under ice-cooling over a period of 10 minutes and then the mixture was stirred for 3.5 hours at room temperature. To the reaction mixture was successively added ice-water and ethyl acetate followed by stirring. The resultant mixture was adjusted to pH 2 with 1 N hydrochloric acid, shaken and then the ethyl acetate layer was separated. The remaining aqueous layer was further extracted with ethyl acetate. After the combined ethyl acetate layers were well shaken with an aqueous solution of sodium bicarbonate, the aqueous layer was separated and thereto was added ethyl acetate. The resultant mixture was adjusted to pH 2 with 2% sulfuric acid and then the precipitates were collected by filtration to give 7β-[2-isopropoxyimino-2-(2-formamidothiazol-4-yl)acetamido]-1-oxadethia-3-cephem-4-carboxylic acid (syn isomer) (529 mg.), mp 171° to 210° C. (dec.). Further, after the separation of the ethyl acetate layer from the filtrate, the remaining aqueous layer was saturated with sodium chloride and then extracted with ethyl acetate. The combined ethyl acetate layers were dried over magnesium sulfate and concentrated. The residue was crystallized in a mixture of ethyl acetate and diethyl ether to give the same object compound (81 mg.).

I.R. (Nujol): 3250, 1785, 1690, 1650, 1620 cm$^{-1}$.

N.M.R. (d$_6$-DMSO, δ): 1.20 (6H, d, J=6 Hz), 4.32 (1H, m), 4.50 (2H, d, J=3 Hz), 5.15 (1H, d, J=4 Hz), 5.72 (1H, d, J=4,9 Hz), 6.46 (1H, t, J=3 Hz), 7.36 (1H, s), 8.52 (1H, s), 9.27 (1H, d, J=9 Hz), 12.80 (1H, broad).

EXAMPLE 20

To a solution of benzyl 7β-[2-methoxyimino-2-(6-formamidopyridin-2-yl)acetamido]-1-oxadethia-3-cephem-4-carboxylate (848 mg.) in methylene chloride (40 ml.) was added anisole (2.88 g.) and thereto was added dropwise a solution of aluminum chloride (1.18 g.) in nitromethane (10 ml.) under ice-cooling. After stirring for 2 hours at room temperature, the reaction mixture was poured into a mixture of ethyl acetate and ice-water. The mixture was adjusted to pH 1 to 2 with 1 N hydrochloric acid and then the ethyl acetate layer was separated therefrom. The remaining aqueous layer was extracted with ethyl acetate and the combined ethyl acetate layers were washed successively with a saturated aqueous solution of sodium bicarbonate (5 ml.×6) and water. To the washings was added ethyl acetate (100 ml.) and the mixture was adjusted to pH 1 with 3 N hydrochloric acid and then extracted with ethyl acetate. To the aqueous layer was added sodium chloride and then the resulting mixture was extracted with ethyl acetate twice. The ethyl acetate extracts were combined, dried over magnesium sulfate and then evaporated. The residue was triturated in a mixture of ethyl acetate and diethyl ether and the precipitates were collected by filtration and then dried over magnesium sulfate to give 7β-[2-methoxyimino-2-(6-formamidopyridin-2-yl)acetamido]-1-oxadethia-3-cephem-4-carboxylic acid (syn isomer) (366 mg.), mp 130° to 160° C. (dec.).

I.R. (Nujol): 3260, 1780, 1720, 1675, 1640 cm$^{-1}$.

N.M.R. (d$_6$-DMSO, δ): 3.92 (3H, s), 4.50 (2H, m), 5.15 (1H, d,), 5.62 (1H, dd, J=4,9 Hz), 6.44 (1H, m), 9.36 (1H, d, J=9 Hz), 6.42 (1H, d, J=8 Hz), 7.46 (1H, d, J=8 Hz), 7.76 (1H, t, J=8 Hz), 9.26 (1H, d, J=8 Hz), 10.56 (1H, d, J=8 Hz).

EXAMPLE 21

A solution of benzyl 7β-[2-methoxyimino-2-(4-aminpyrimidin-2-yl)acetamido]-1-oxadethia-3-cephem-4-carboxylate (syn isomer) (400 mg.) in a mixture of ethanol (8 ml.) and ethyl acetate (4 ml.) was hydrogenated over palladium-charcoal (300 mg.) at atmospheric pressure for 90 minutes. The reaction mixture was filtered through celite and the filter was washed with a mixture of methanol and water. The filtrate and washing were combined and evaporated to dryness. The residue was triturated with ethanol to give crystals of 7β-[2-methoxyimino-2-(4-aminopyrimidine-2-yl)acetamido]-1-oxadethia-3-cephem-4-carboxylic acid (syn isomer) (234 mg.), which is decomposed till 230° C.

I.R. (Nujol): 3460, 3350, 3260, 1780, 1630 cm$^{-1}$.

N.M.R. (DMSO-d$_6$, δ): 3.94 (3H, s), 4.53 (2H, m), 5.15 (1H, d, J=4 Hz), 5.65 (1H, dd, J=4 and 9 Hz), 6.41 (1H, d, J=6 Hz), 6.44 (1H, m), 7.0 (2H, broad s), 8.10 (1H, d, J=6 Hz), 9.11 (1H, d, J=9 Hz).

EXAMPLE 22

To a solution of benzyl 7β-[2-methoxyimino-2-(5-amino-1,2,4-thiadiazol-3-yl)acetamido]-1-oxadethia-3-cephem-4-carboxylate (syn isomer) (889 mg.) in methylene chloride (15 ml.) were added anisole (3.2 ml.) and a solution of aluminum chloride (1.29 g.) in nitromethane (7 ml.) under ice-cooling and the mixture was stirred for 1.8 hours at ambient temperature. After addition of a solution of aluminum chloride (266 mg.) in nitromethane (1.5 ml.), the resulting solution was stirred for an additional 30 minutes. The reaction mixture was poured into a mixture of ethyl acetate and ice-water and then the aqueous layer was separated. The organic layer was washed with a dil. aqueous solution of sodium bicarbonate and the washing was adjusted to pH 3. The aqueous layer and the washing were combined, saturated with sodium chloride and extracted with n-butanol. After evaporation of the extract, methanol was added to the residue and the resulting mixture was filtered and then the filtrate was concentrated. To the concentrate was added an aqueous solution of sodium bicarbonate and the mixture was filtered. The filtrate was adjusted to pH 3 with 1 N hydrochloric acid and subjected to column chromatography (non-ion adsorption resin, Diaion HP20 prepared by Mitsubishi Chemical Industries, 70 ml.) and the column was washed successively with water and a mixture of methanol and water (1:1). The fractions containing the desired compound were collected and evaporated. The residue was washed with diethyl ether and dried to give a powder of 7β-[2-methoxyimino-2-(5-amino-1,2,4-thiadiazol-3-yl)acetamido]1-oxadethia-3-cephem-4-carboxylic acid (syn isomer) (310 mg.), which is decomposed till 220° C.

I.R. (Nujol): 3400, 3350, 3260, 1780, 1700, 1640 cm$^{-1}$.

N.M.R. (DMSO-d$_6$, δ): 3.94 (3H, s), 4.53 (2H, d, J=3 Hz), 5.17 (1H, d, J=4 Hz), 5.69 (1H, dd, J=4 and 9 Hz), 6.50 (1H, t, J=3 Hz), 8.10 (2H, broad s), 9.29 (1H, d, J=9 Hz).

EXAMPLE 23

The following compounds were obtained according to the similar manners to those of Example 17 to 22.

(1) 7β-[2-Methoxyimino-2-(2-aminothiazol-4-yl)acetamido]-1-oxadethia-3-cephem-4-carboxylic acid hydrochloride (syn isomer).
I.R. (Nujol): 3400–2400, 1780, 1730, 1680, 1640 cm$^{-1}$.

(2) 7β-[2-Methoxyimino-2-(2-aminothiazol-4-yl)acetamido]1-oxadethia-3-cephem-4-carboxylic acid (syn isomer), powder.
I.R. (Nujol): 3600–2400, 1785, 1720, 1660 cm$^{-1}$.

(3) 7β-[2-n-Butoxyimino-2-(2-formamidothiazol-4-yl)acetamido]-1-oxadethia-3-cephem-4-carboxylic acid (syn isomer), which is decomposed up to 165° C.
I.R. (Nujol): 3600–2500, 1795, 1690, 1670 cm$^{-1}$.
N.M.R. (d$_6$-DMSO, δ): 0.90 (3H, t, J=6 Hz), 1.1–1.8 (4H, m), 4.08 (2H, t, J=6 Hz), 4.50 (2H, m), 5.14 (1H, d, J=4 Hz), 5.58 (1H, dd, J=4, 8 Hz), 6.44 (1H, m), 7.34 (1H, s), 8.48 (1H, s), 9.32 (1H, d, J=8 Hz).

(4) 7β-[2-n-Pentyloxyimino-2-(2-formamidothiazol-4-yl)acetamido]-1-oxadethia-3-cephem-4-carboxylic acid (syn isomer), mp 142° to 147° C. (dec.).
I.R. (Nujol): 3400–2500, 1790, 1725, 1680 cm$^{-1}$.
N.M.R. (d$_6$-DMSO, δ): 0.90 (3H, t, J=6 Hz), 1.1–1.9 (6H, m), 4.10 (2H, t, J=6 Hz), 4.57 (2H, d, J=2 Hz), 5.23 (1H, d, J=4 Hz), 5.66 (1H, dd, J=4,8 Hz), 6.50 (1H, t, J=2 Hz), 7.40 (1H, s), 8.55 (1H, s), 9.37 (1H, d, J=8 Hz).

(5) 7β-(2-Methoxyimino-2-phenylacetamido)-1-oxadethia-3-cephem-4-carboxylic acid (syn isomer) (crystals), mp 80° to 95° C. (dec.).
I.R. (Nujol): 3250, 1780, 1720, 1660, 1630 cm$^{-1}$.
N.M.R. (d$_6$-DMSO, δ): 3.95 (3H, s), 4.56 (2H, d, J=3 Hz), 5.21 (1H, d, J=4 Hz), 5.66 (1H, dd, J=4,8 Hz), 6.50 (1H, t, J=3 Hz), 7.4–7.7 (5H, m), 9.50 (1H, d, J=8 Hz).

(6) 7β-[2-(2-Formamidothiazol-4-yl)glyoxylamido]-1-oxadethia-3-cephem-4-carboxylic acid, mp 200° to 220° C. (dec.).
I.R. (Nujol): 3140, 1780, 1700, 1670 cm$^{-1}$.
N.M.R. (d$_6$-DMSO, δ): 4.56 (2H, m), 5.20 (1H, d, J=4 Hz), 5.67 (1H, dd, J=4, 9 Hz), 6.53 (1H, m), 8.50 (1H, s), 8.64 (1H, s), 9.60 (1H, d, J=9 Hz), 12.80 (1H, broad s).

(7) 7β-[2-Methoxyimino-2-(5,6-dihydro-1,4-oxathiin-2-yl)acetamido]-1-oxadethia-3-cephem-4-carboxylic acid (anti isomer), mp 163° to 165° C. (dec.).
I.R. (Nujol): 3300, 1780, 1720, 1660, 1635 cm$^{-1}$.
N.M.R. (d$_6$-DMSO, δ): 3.00 (2H, m), 3.84 (3H, s), 4.11 (2H, m), 4.46 (2H, d, J=3 Hz), 5.05 (1H, d, J=4 Hz), 5.49 (1H, dd, J=4,9 Hz), 6.33 (1H, s), 6.40 (1H, t, J=3 Hz), 8.83 (1H, d, J=9 Hz).

(8) 7β-[2-(1H-1,2,3,4-Tetrazol-1-yl)acetamido]-1-oxadethia-3-cephem-4-carboxylic acid, mp 164° to 167° C.
I.R. (Nujol): 3340, 1790, 1720, 1670 cm$^{-1}$.
N.M.R. (d$_6$-DMSO, δ): 4.60 (2H, d, J=3 Hz), 5.18 (1H, d, J=4 Hz), 5.43 (2H, s), 5.60 (1H, dd, J=4,9 Hz), 6.57 (1H, t, J=3 Hz), 9.37 (1H, d, J=9 Hz), 9.42 (1H, s).

(9) 7β-[2-Methoxyimino-2-(2-furyl)acetamido]-1-oxadethia-3-cephem-4-carboxylic acid (syn isomer), mp 197° C. (dec.).
I.R. (Nujol): 3270, 1750, 1720, 1660, 1630.
N.M.R. (d$_6$-DMSO, δ): 3.92 (3H, s), 4.57 (2H, d, J=3 Hz), 5.21 (1H, d, J=4 Hz), 5.63 (1H, dd, J=4,8 Hz), 6.51 (1H, t, J=3 Hz), 6.69 (2H, m), 7.86 (1H, m), 9.50 (1H, d).

(10) 7β-[2-Ethoxyimino-2-(2-aminothiazol-4-yl)acetamido]-1-oxadethia-3-cephem-4-carboxylic acid (syn isomer), which is gradually decomposed from 150° C.

(11) 7β-[2-Isopropoxyimino-2-(2-aminothiazol-4-yl)acetamido]-1-oxadethia-3-cephem-4-carboxylic acid hydrochloride (syn isomer), which is softened at 65° to 70° C. and gradually decomposed up to 140° C.

(12) 7β-[2-n-Butoxyimino-2-(2-aminothiazol-4-yl)acetamido]-1-oxadethia-3-cephem-4-carboxylic acid (syn isomer), dp>200° C.

(13) 7β-[2-n-Pentyloxyimino-2-(2-aminothiazol-4-yl)acetamido]-1-oxadethia-3-cephem-4-carboxylic acid hydrochloride (syn isomer), mp 118° to 124° C. (dec.).

(14) 7β-[2-Methoxyimino-2-(6-aminopyridin-2-yl)acetamido]-1-oxadethia-3-cephem-4-carboxylic acid hydrochloride (syn isomer) (powder), mp 100° to 140° C. (dec.).

(15) 7β-[2-(2-Aminothiazol-4-yl)glyoxylamido]-1-oxadethia-3-cephem-4-carboxylic acid, dp>240° C.

(16) 7β-(D,L-2-sulfo-2-phenylacetamido)-1-oxadethia-3-cephem-4-carboxylic acid (amorphous solid).
I.R. (KBr): 1790, 1730, 1680 cm$^{-1}$.
N.M.R. (DMSO-d$_6$, δ): 4.44–4.60 (3H, m), 5.12 (1H, m), 5.72 (1H, dd, J=4,8 Hz), 6.46 (1H, m), 7.12–7.56 (5H, m), 8.88 and 8.94 (1H, two d, J=8 Hz).

(17) 7β-[2-Allyloxyimino-2-(2-formamidothiazol-4-yl)acetamido]-1-oxadethia-3-cephem-4-carboxylic acid (syn isomer).
I.R. (Nujol): 3450, 3330, 3170, 1770, 1690, 1645, 1635, 1620, 1540 cm$^{-1}$.
N.M.R. (DMSO-d$_6$, δ): 4.7 (4H, m), 5.21 (1H, d, J=4 Hz), 5.2–6.25 (4H, m), 6.50 (1H, m), 7.40 (1H, s), 8.54 (1H, s), 9.45 (1H, d, J=8 Hz), 12.70 (1H, s).

(18) 7β-[2-(2-Propynyloxyimino)-2-(2-formamidothiazol-4-yl)acetamido]-1-oxadethia-3-cephem-4-carboxylic acid (syn isomer), crystalline solid.
I.R. (Nujol): 3250, 1780, 1720, 1680, 1660 cm$^{-1}$.
N.M.R. (DMSO-d$_6$, δ): 3.48 (1H, t, J=2.5 Hz), 4.54 (2H, d, J=2 Hz), 4.75 (2H, d, J=2.5 Hz), 5.17 (1H, d, J=4 Hz), 5.60 (1H, dd, J=4 and 8 Hz), 6.48 (1H, t, J=2 Hz), 7.43 (1H, s), 8.54 (1H, s), 9.50 (1H, d, J=8 Hz), 12.68 (1H, s).

(19) 7β-[2-Benzyloxyimino-2-(2-formamidothiazol-4-yl)acetamido]-1-oxadethia-3-cephem-4-carboxylic acid (syn isomer), crystalline solid.
I.R. (Nujol): 3250, 1780, 1670, 1540 cm$^{-1}$.
N.M.R. (DMSO-d$_6$, δ): 4.55 (2H, m), 5.20 (1H, d, J=4 Hz), 5.21 (2H, s), 5.65 (1H, dd, J=4 and 8 Hz), 6.50 (1H, m), 7.39, 7.40 (6H, two s), 8.55 (1H, s), 9.53 (1H, d, J=8 Hz), 12.67 (1H, s).

(20) 7β-Amino-1-oxadethia-3-cephem-4-carboxylic acid.
I.R. (Nujol): 2700–2270, 2120, 1805, 1630, 1540, 1505 cm$^{-1}$.

(21) 7β-[2-Allyloxyimino-2-(2-aminothiazol-4-yl)acetamido]-1-oxadethia-3-cephem-4-carboxylic acid (syn isomer).
I.R. (Nujol): 3300, 1780, 1660, 1540 cm$^{-1}$.

(22) 7β-[2-(2-Propynyloxyimino)-2-(2-aminothiazol-4-yl)acetamido]-1oxadethia-3-cephem-4-carboxylic acid hydrochloride (syn isomer), which is gradually decomposed with coloration till 160° C.

(23) 7β-[2-Benzyloxyimino-2-(2-aminothiazol-4-yl)acetamido]-1-oxadethia-3-cephem-4-carboxylic acid (syn isomer), mp 150° to 170° C. (gradually decomposed with coloration).

(24) 7α-Methoxy-7β-[2-methoxyimino-2-(2-formamidothiazol-4-yl)acetamido]-1-oxadethia-3-cephem-4-carboxylic acid (syn isomer), amorphous solid.

N.R.R. (acetone-d$_6$, δ): 3.58 (3H, s), 3.97 (3H, s), 4.68 (2H, m), 5.16 (1H, s), 6.40 (1H, t, J=3 Hz), 7.60 (1H, s), 8.70 (1H, s), 8.75 (1H, s).

(25) 7α-Methoxy-7β-[2-(2-formamidothiazol-4-yl)acetamido]-1-oxadethia-3-cephem-4-carboxylic acid, amorphous solid.

I.R. (Nujol): 3290, 3150, 1765, 1680 cm$^{-1}$.

N.M.R. (Acetone-d$_6$, δ): 3.45 (3H, s), 3.75 (2H, s), 4.53 (2H, d, J=3 Hz), 5.05 (1H, s), 6.50 (1H, t, J=3 Hz), 7.05 (1H, s), 8.16 (1H, s), 8.65 (1H, s).

(26) 7α-Methoxy-7β-[2-methoxyimino-2-(2-aminothiazol-4-yl)acetamido]-1-oxadethia-3-cephem-4-carboxylic acid hydrochloride (syn isomer).

I.R. (Nujol): 1780, 1720, 1680, 1630 cm$^{-1}$.

(27) 7α-Methoxy-7β-[2-(2-aminothiazol-4-yl)acetamido]-1-oxadethia-3-cephem-4-carboxylic acid hydrochloride, powder.

I.R. (KBr): 1780, 1700, 1630 cm$^{-1}$.

(28) 7β-[2-Eethoxyimino-2(2-formamidothiazol-4-yl)acetamido]-1-oxadethia-3-cephem-4-carboxylic acid (syn isomer), crystal, mp. 132° to 139° C.

I.R. (Nujol): 3200, 3090, 3040, 1770, 1720, 1670, 1650 cm$^{-1}$.

N.M.R. (DMSO-d$_6$ δ): 1.23 (3H, t, J=7 Hz), 4.17 (2H, q, J=7 Hz), 4.55 (2H, m), 5.20 (1H, d, J=4 Hz), 5.66 (1H, dd, J=4 and 8 Hz), 6.50 (1H, m), 7.40 (1H, s), 8.56 (1H, s), 9.38 (1H, d, J=8 Hz), 12.7 (1H, broad).

(29) 7β-[2-Ethoxyimino-2-(2-aminothiazol-4-yl)acetamido]-1-oxadethia-3-cepham-4-carboxylic acid hydrochloride (syn isomer), crystal, mp 150° to 158° C. (dec.).

(30) 7β-[2-(2-Formamidothiazol-4-yl)acetamido]-1-oxadethia-3l -cephem-4-carboxylic acid.

I.R. (Nujol): 3280, 3100, 1770, 1720, 1695, 1650 cm$^{-1}$.

N.M.R. (DMSO-d$_6$, δ): 3.62 (2H, s), 4.53 (2H, m), 5.14 (1H, d, J=4 Hz), 5.54 (1H, dd, J=4 and 8.5 Hz), 6.50 (1H, t, J=2 Hz), 6.98 (1H, s), 8.52 (1H, s), 8.88 (1H, d, J=8.5 Hz), 12.3 (1H, broad).

(31) 7β-[2-(2-Aminothiazol-4-yl)acetamido]-1-oxadethia-3-cephem-4-carboxylic acid.

I.R. (Nujol): 3540, 3480, 3250, 3050, 1770, 1660 cm$^{-1}$.

EXAMPLE 24

A solution of conc. hydrochloric acid (170 mg.) in methanol (0.6 ml.) was added dropwise to a solution of 7β-[2-methoxyimino-2-(2-formamidothiazol-4-yl)acetamido]-1-oxadethia-3-cephem-4-carboxylic acid (syn isomer) (170 mg.) in methanol (3 ml.) with stirring at ambient temperature, after which the mixture was stirred for 4 hours at ambient temperature. Methanol was concentrated to about half a volume and diethyl ether (30 ml.) was added thereto. Precipitating powder was collected by filtration, washed with diethyl ether and dried under reduced pressure to give 7β-[2-methoxyimino-2-(2-aminothiazol-4-yl)acetamido]-1-oxadethia-3-cephem-4-carboxylic acid hydrochloride (syn isomer) (95 mg.).

I.R. (Nujol): 3400–2400, 1780, 1730, 1680, 1640 cm$^{-1}$.

N.M.R. (d$_6$-DMSO, δ): 3.95 (3H, s), 4.61 (2H, m), 5.18 (1H, d, J=4 Hz), 5.55 (1H, dd, J=4, 9 Hz), 6.51 (1H, m), 6.95 (1H, s), 9.59 (1H, d, J=9 Hz).

EXAMPLE 25

7β-[2-Isopropoxyimino-2-(2-formamidothiazol-4-yl)acetamido]-1-oxadethia-3-cephem-4-carboxylic acid (syn isomer) (550 mg.) was suspended in methanol (25 ml.) under ice-cooling and thereto was added 1.68 mM solution (1.4 ml.) of conc.hydrochloric acid in methanol at the same temperature, followed by stirring for 2 hours and 50 minutes at room temperature. The reaction mixture was concentrated under reduced pressure to about onefourth of the original volume, and thereto was added bit by bit diethyl ether. The precipitates were collected by filtration, washed with diethyl ether and then dried over phosphorus pentoxide to give 7β-[2-isopropoxyimino-2-(2-aminothiazol-4-yl)acetamido]-1-oxadethia-3-cephem-4-carboxylic acid hydrochloride (syn isomer) (508 mg.), which was softened at 65° to 70° C. and gradually decomposed up to 140° C.

I.R. (Nujol): 1765, 1700, 1660, 1630 cm$^{-1}$.

N.M.R. (d$_6$-DMSO, δ): 1.23 (6H, d, J=6 Hz), 4.34 (1H, m), 4.50 (2H, m), 5.10 (1H, d, J=4 Hz), 5.48 (1H, dd, J=4, 8 Hz), 6.44 (1H, m), 6.86 (1H, s), 9.41 (1H, d, J=8 Hz).

EXAMPLE 26

The following compounds were prepared according to the similar manner to those of Examples 24 and 25.

(1) 7β-[2-Ethoxyimino-2-(2-aminothiazol-4yl-)acetamido]-oxadethia-3-cephem-4-carboxylic acid (syn isomer), which is gradually decomposed from 150° C.

(2) 7β-[2-n-Butoxyimino-2-(2-aminothiazol-4-yl)acetamido]-1-oxadethia-3-cephem-4-carboxylic acid (syn isomer), dp>200° C.

I.R. (Nujol): 3330, 1785, 1670, 1630 cm$^{-1}$.

N.M.R. (d$_6$-DMSO, δ): 0.90 (3H, t, J=6 Hz), 1.1–1.8 (4H, m), 4.05 (2H, t, J=6 Hz), 4.54 (2H, m), 5.15 (1H, d, J=4 Hz), 5.58 (1H, dd, J=4,8 Hz), 6.48 (1H, m), 6.75 (1H, s), 9.28 (1H, d, J=8 Hz).

(3) 8β-[2-n-Pentyloxyimino-2-(2-aminothiazol-4-yl)acetamido]-1-oxadethia-3-cephem-4-carboxylic acid hydrochloride (syn isomer) (powder), mp 118° to 124° C. (dec.).

I.R. (Nujol): 3400–2400, 1790, 1730, 1680, 1630 cm$^{-1}$.

N.M.R. (d$_6$-DMSO, δ): 0.90 (3H, t, J=6 Hz), 1.0–1.9 (6H, m), 4.17 (2H, t, J=6 Hz), 4.58 (2H, m), 5.20 (1H, d, J=4 Hz), 5.56 (1H, dd, J=4,8 Hz), 6.52 (1H, m), 6.97 (1H, s), 9.56 (1H, d, J=8 Hz).

(4) 7β-[2-Methoxyimino-2-(6-aminopyridin-2-yl)acetamido]-1-oxadethia-3-cephem-4-carboxylic acid hydrochloride (syn isomer) (powder), mp 100° to 140° C. (dec.).

I.R. (Nujol): 1780 cm$^{-1}$.

N.M.R. (d$_6$-DMSO, δ): 4.12 (3H, s), 4.60 (2H, d, J=3 Hz), 5.23 (1H, d, J=4 Hz), 5.63 (1H, dd, J=4,8 Hz), 6.50 (1H, t, J=3 Hz), 6.78 (1H, d, J=8 Hz), 7.19 (1H, d, J=9 Hz), 7.98 (1H, dd, J=8,9 Hz), 9.73 (1H, d, J=8 Hz).

(5) 7β-[2-(2-Aminothiazol-4-yl)glyoxlamido]-1-oxadethia-3-cephem-4-carboxylic acid, dp¢240° C.

I.R. (Nujol): 3350, 1780, 1700, 1650 cm$^{-1}$.

N.M.R. (d$_6$-DMSO, δ): 4.50 (2H, m), 5.14 (1H, d, J=4 Hz), 5.54 (1H, dd, J=4,8 Hz), 6.45 (1H, m), 7.36 (2H, broad s), 7.84 (1H, s), 9.42 (1H, d, J=8 Hz).

(6) 7β-[2-Methoxyimino-2-(2-aminothiazol-4-yl)acetamido]-1-oxadethia-3-cephem-4-carboxylic acid (syn isomer), powder.

I.R. (Nujol): 3600–2400, 1785, 1720, 1660 cm$^{-1}$.

(7) 7β-[2-Allyloxyimino-2-(2-aminothiazol-4-yl)acetamido]-1-oxadethia-3-cephem-4-carboxylic acid (syn isomer).

I.R. (Nujol): 3300, 1780, 1660, 1540 cm$^{-1}$.

N.M.R. (DMSO-d$_6$, δ): 4.6 (4H, m), 5.19 (1H, d, J=4 Hz), 5.1–6.2 (4H, m), 6.50 (1H, m), 6.80 (1H, s), 7.2 (2H, broad), 9.35 (1H, d, J=8 Hz).

(8) 7β-[2-(2-Propynyloxyimino)-2-(2-aminothiazol-4-yl)acetamido]-1-oxadethia-3-cephem-4-carboxylic acid hydrochloride (syn isomer), which is gradually decomposed with coloration till 160° C.

I.R. (Nujol): 1760, 1700, 1660, 1620 cm$^{-1}$.

N.M.R. (DMSO-d$_6$, δ): 3.58 (1H, t, J=2.5 Hz), 4.58 (2H, m), 4.84 (2H, d, J=2.5 Hz), 5.20 (1H, d, J'4 Hz), 5.56 (1H, dd, J=4 and 8 Hz), 6.51 (1H, m), 7.00 (1H, s), 8.2 (broad), 9.61 (1H, d, J=8 Hz).

(9) 7β-[2-Benzyloxyimino-2-(2-aminothiazol-4-yl)acetamido]-1-oxadethia-3-cephem-4-carboxylic acid (syn isomer), mp 150° to 170° C. (gradually decomposed with coloration).

I.R. (Nujol): 3250, 3080, 1780, 1660, 1630, 1580 cm$^{-1}$.

N.M.R. (DMSO-d$_6$, δ): 4.52 (2H, m), 5.18 (3H, s and d), 5.58 (1H, dd, J=4 and 8 Hz), 6.48 (1H, m), 6.82 (1H, s), 7.38 (5H, s), 9.48 (1H, d, J=8 Hz).

(10) Benzyl 7β-[2-methoxyimino-2-(4-aminopyrimidin-2-yl)acetamido]-1-oxadethia-3-cephem-4-carboxylate (syn isomer), mp 120° to 137° C.

(11) Benzyl 7β-[2-methoxyimino-2-(5-amino-1,2,4-thiadiazol-3-yl)acetamido]-2-oxadethia-3-cephem-4-carboxylate (syn isomer).

I.R. (Nujol): 3450, 3360, 3240, 1790, 1735 1675 cm$^{-1}$.

(12) 7β-[2-Methoxyimino-2-(4-aminoyrimidin-2-yl)acetamido]-1-oxadethia-3-cephem-4-carboxylic acid (syn isomer), crystal.

I.R. (Nujol): 3460, 3350, 3260, 1780, 1630 cm$^{-1}$.

(13) 7β-[2-Methoxyimino-2-(5-amino-1,2,4-thiadiazol-3-yl)acetamido]-1-oxadethia-3-cephem-4-carboxylic acid (syn isomer), powder.

I.R. (Nujol): 3400, 3350, 3260, 1780, 1700, 1640 cm$^{-1}$.

(14) 7α-Methoxy-7β-[2-methoxyimino-2-(2-aminothiazol-4-yl)acetamido]-1-oxadethia-3-cephem-4-carboxylic acid ydrochloride (syn isomer).

I.R. (Nujol): 1780, 1720, 1680, 1630 cm$^{-1}$.

N.M.R. (DMSO-d$_6$, δ): 3.50 (3H, s), 4.00 (3H, s), 4.68 (2H, m), 5.20 (1H, s), 6.55 (1H, m), 7.04 (1H, s), 8.5 (broad), 11.75 (1H, s).

(15) 7α-Methoxy-7β-[2-(2-aminothiazol-4-yl)acetamido]-1-oxadethia-3-cephem-4-carboxylic acid hydrochloride, powder.

I.R. (KBr): 1780, 1700, 1630 cm$^{-1}$.

N.M.R. (DMSO-d$_6$, δ): 3.44 (3H, s), 3.67 (2H, s), 4.52 (2H, m), 5.08 (1H, s), 6.50 (1H, t, J=3 Hz), 6.73 (1H, s), 11.0 (1H, s).

(16) 7β-[2-Ethoxyimino-2-(2-aminothiazol-4-yl)acetamido]-1-oxadethia-3-cephem-4-carboxylic acid hydrochloride (syn isomer), crystal, mp 150° to 158° C. (dec.).

N.M.R. (DMSO-d$_6$, δ): 1.27 (3H, t, J=7 Hz), 4.20 (2H, q, J=7 Hz), 4.57 (2H, m), 5.20 (1H, d, J=4 Hz), 5.60 (1H, dd, J=4 and 8 Hz), 6.53 (1H, m), 6.97 (1H, s), 9.80 (1H, d, J=8 Hz).

(17) 7β-[2-(2-Aminothiazol-4-yl)acetamido]-1-oxadethia-3-cephem-4-carboxylic acid.

I.R. (Nujol): 3540, 3480, 3250, 3050, 1770, 1660 cm$^{-1}$.

N.M.R. (DMSO-d$_6$, δ): 3.40 (2H, s), 4.53 (2H, m), 5.09 (1H, d, J=4 Hz), 5.51 (1H, dd, J=4 and 9 Hz), 6.27 (1H, s), 6.49 (1H m), 6.93 (2H, broad), 8.67 (1H, d, J=9 Hz).

EXAMPLE 27

Anisole (3.09 g.) was added to a solution of benzyl 7β-[2-methoxyimino-2-(2-formamidothiazol-4-yl)acetamido]-1-oxadethia-3-cephem-4-carboxylate (syn isomer) (1.05 g.) in methylene chloride (100 ml.), and then a solution of aluminum chloride (2.66 g.) in nitromethane (30 ml.) was added dropwise thereto under ice-cooling and stirring. The resulting mixture was stirred for 15 minutes under ice-cooling and for 4.5 hours at ambient temperature. The reaction mixture was diluted with ethyl acetate (400 ml.) and extracted twice with 5% hydrochloric acid (20 ml.). The hydrochloric acid layer was extracted with n-butanol (30 ml.×1 and 15 ml.×3), and n-butanol was distilled off under reduced pressure from the extracts to give oily residue (760 mg.). The oil was dissolved in water (20 ml.), and then the solution was adjusted to about pH 3 with 5% aqueous solution of sodium bicarbonate. The resulting solution was subjected to column chromatography on Diaion HP-20 resin (Trademark: prepared by Mitsubishi Chemical Industries Ltd.). After the column was developed with water (200 ml.) to remove impure materials, the column was eluted with 50% aqueous methanol. The fractions containing the object compound were collected and concentrated. The residue was pulverized with diethyl ether (30 ml.) to give powder of 7β-[2-methoxyimino-2-(2-aminothiazol-4-yl)acetamido]-1-oxadethia-3-cephem-4-carboxylic acid (syn isomer) (315 mg.).

I.R. (Nujol): 3600–2400, 1785, 1720, 1660 cm$^{-1}$.

N.M.R. (d$_6$-DMSO, δ): 3.88 (3H, s), 4.55 (2H, m), 5.17 (1H, d, J=4 Hz), 5.58 (1H, dd, J=4, 9 Hz), 6.50 (1H, m), 6.78 (1H, s), 9.34 (1H, d, J=9 Hz).

EXAMPLE 28

To a solution of benzyl 7β-[2-ethoxyimino-2-(2-formamidothiazol-4-yl)acetamido]-1-oxadethia-3-cephem-4-carboxylate (syn isomer) (1.52 g.) in methylene chloride (30 ml.) was added anisole (4.96 ml.) under ice-cooling. To the mixture was added dropwise a mixture of aluminum chloride (2.02 g.) in nitromethane (13 ml.) and stirring for an hour at room temperature. The reaction mixture was poured into a mixture of ethyl acetate (100 ml.) and a solution of 1N hydrochloric acid (30 ml.) in ice-water (100 ml.) followed by stirring and thereto was added ethyl acetate (100 ml.). The aqueous layer was separated, washed with ethyl acetate (50 ml.×2), adjusted to pH 4 with a saturated aqueous solution of sodium bicarbonate and then shaken with n-butanol. After the n-butanol layer was separated and concentrated, the residue was pulverized in diethyl ether and collected by filtration to give the crude product (437 mg.). The same product (584 mg.) was further obtained from the remaining aqueous layer and the diethyl ether filtrate. Thus obtained product was suspended in water (15 ml.), adjusted to pH 7 to 8 with an aqueous solution of sodium bicarbonate and then filtered. The filtrate was adjusted to pH 3 with 1 N hydrochloric acid and subjected to column chromatography (non-ion adsorption resin, diaion HP20 prepared by Mitsubishi Chemical Industries), and eluted first with water and then with a mixture of water and methanol (1:1). Fractions containing the object compound were evaporated and the residue was triturated in diethyl ether. The precipitates were collected by filtration, washed with diethyl ether and then dried to give crystals of 7β-[2-ethoxyimino-2-(2-aminothiazol-4-yl)acetamido]-1-oxadethia-3-cephem-4-carboxylic acid (syn isomer) (336 mg.), which was gradually decomposed from 150° C.

N.M.R. (d$_6$-DMSO, α): 1.20 (3H, t, J=6 Hz), 4.06 (2H, q, J=6 Hz), 4.52 (2H, m), 5.14 (1H, d, J=4 Hz), 5.56 (1H, dd, J=4,8 Hz), 6.46 (1H, m), 6.74 (1H, s), 7.18 (2H, broad s), 9.26 (1H, d, J=8 Hz).

EXAMPLE 29

The following compounds were prepared according to the similar manner to those of Examples 27 and 28

(1) 7β-[2-Isopropoxyimino-2-(2-aminothiazol-4-yl)acetamido]-1-oxadethia-3-cephem-4-carboxylic acid hydrochloride (syn isomer), which is softened at 65 to 70° C. and gradually decomposed up to 140° C.

(2) 7β-[2-n-Butoxyimino-2-(2-aminothiazol-4-yl)acetamido]-1-oxadethia-3-cephem-4-carboxylic acid (syn isomer), dp>200° C.

(3) 7β-[2-n-Pentyloxyimino-2-(2-aminothiazol-4-yl)acetamido]-1-oxadethia-3-cephem-4-carboxylic acid hydrochloride (syn isomer), mp 118° to 124° C. (dec.).

(4) 7β-[2-Methoxyimino-2-(6-aminopyridin-2-yl)acetamido]-1-oxadethia-3-cephem-4-carboxylic acid hydrochloride (syn isomer) (powder), mp 100° to 140° C. (dec.).

(5) 7β-[2-(2-Aminothiazol-4-yl)glyoxylamido]-1-oxadethia-3-cephem-4-carboxylic acid, dp>240° C.

(6) 7β-[2-Methoxyimino-2-(2-aminothiazol-4-yl)acetamido]-1-oxadethia-3-cephem-4-carboxylic acid hydrochloride (syn isomer).

I.R. (Nujol): 3400–2400, 1780, 1730, 1680, 1640 cm$^{-1}$.

(7) 7β-[2-Methoxyimino-2-(4-aminopyrimidin-2-yl)acetamido]-1-oxadethia-3-cephem-4-carboxylic acid (syn isomer), crystal.

I.R. (Nujol): 3460, 3350, 3260, 1780, 1630 cm$^{-1}$.

(8) 7β-[2-Methoxyimino-2-(5-amino-1,2,4-thiadiazol-3-yl)acetamido]-1-oxadethia-3-cephem-4-carboxylic acid (syn isomer), powder.

I.R. (Nujol): 3400, 3350, 3260, 1780, 1700, 1640 cm$^{-1}$.

(9) 7β-[2-Allyloxyimino-2-(2-aminothiazol-2-(2-aminothiazol-4-yl)acetamido]-1-oxadethia-3-cephem-4-carboxylic acid (syn isomer).

I.R. (Nujol): 3300, 1780, 1660, 1540 cm$^{-1}$.

(10) 7β-[2-(2-Propynyloxyimino)-2-(2-aminothiazol-4-yl)acetamido]-1-oxadethia-3-cephem-4-carboxylic acid hydrochloride (syn isomer), which is gradually decomposed with coloration till 160° C.

(11) 7β-[2-Benzyloxyimino-2-(2-aminothiazol-4-yl)acetamido]-1-oxadethia-3-cephem-4-carboxylic acid (syn isomer), mp 150° to 170° C. (gradually decomposed with coloration).

(12) 7α-Methoxy-7β-[2-methoxyimino-2-(2-aminothiazol-4-yl)acetamido]-1-oxadethia-3-cephem-4-carboxylic acid hydrochloride (syn isomer).

I.R. (Nujol): 1780, 1720, 1680, 1630 cm$^{-1}$.

(13) 7α-Methoxy-7β-[2-(2-aminothiazol-4-yl)acetamido]-1-oxadethia-3-cephem-4-carboxylic acid hydrochloride, powder.

I.R. (KBr): 1780, 1700, 1630 cm$^{-1}$.

(14) 7β-[2-Ethoxyimino-2-(2-aminothiazol-4-yl)acetamido]-1-oxadethia-3-cephem-4-carboxylic acid hydrochloride (syn isomer), crystal, mp 150° to 158° C. (dec.).

(15) 7β-[2-(2-Aminothiazol-4-yl)acetamido]-1-oxadethia-3-cephem-4-caboxylic acid.

I.R. (Nujol): 3540, 3480, 3250, 3050, 1770, 1660 cm$^{-1}$.

EXAMPLE 30

To a solution of benzyl 7β-[2-methoxyimino-2-(5,6-dihydro-1,4-oxathiin-2-yl)acetamido]-1-oxadethia-3-cephem-4-carboxylate (syn isomer) (168 mg.) in methylene chloride (5 ml.) was added anisole (630 mg.) and thereto was added a solution of aluminum chloride (244 mg.) in nitromethane (1.5 ml.) under ice-cooling followed by stirring for 20 minutes at the same temperature. To the reaction mixture was successively added ice water and ethyl acetate, and the resultant mixture was acidified with 1N hydrochloric acid and then shaken. The ethyl acetate layer was separated, washed with an aaqueous solution of sodium chloride, dried over magnesium and then concentrated. The residue was subjected to thin layer chromatography using a mixture of benzene and acetone (4:1) as the developing solvent to give crystals of benzyl 7β-[2-methoxyimino-2-(5,6-dihydro-1,4-oxathiin-2-yl)acetamido]-1-oxadethia-3-cephem-4-carboxylate (anti isomer) (64.4 mg.), mp 142° to 144° C.

I.R. (Nujol): 3225, 1780, 1735, 1660, 1630 cm$^{-1}$.

N.M.R. (d$_6$-DMSO, δ): 3.00 (2H, m), 3.86 (3H, s), 4.12 (2H, m), 4.49 (2H, m), 5.10 (1H, d, J=4 Hz), 5.52 (1H, dd, J=4,9 Hz), 5.24 (2H, s), 6.33 (1H, s), 6.56 (1H, m), 7.36 (5H, m), 8.81 (1H, d, J=9 Hz).

What we claim is:

1. A compound of the formula:

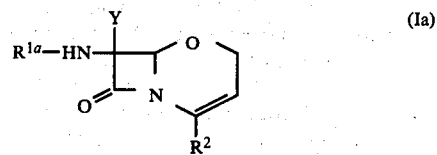

(Ia)

wherein
R$^{1a}$ is a group of the formula:

R$^3$-A-COin which
R$^3$ is aminothiazolyl, aminothiadiazolyl, aminopyridyl or aminopyrimidinyl, and
A is
  lower alkoxyiminomethylene,
  lower alkenyloxyiminomethylene,
  lower alkynyloxyiminomethylene or
  phenyl(lower)alkoxyiminomethylene;
R$^2$ is carboxy or a protected carboxy; and
Y is hydrogen or lower alkoxy, and pharmaceutically acceptable salts thereof.

2. The compound of claim 1 which is the syn isomer.

3. The compound of claim 2 wherein R$^2$ is carboxy and Y is hydrogen or methoxy.

4. The compound of claim 3, wherein
R$^{1a}$ is 2-lower alkoxyimino-2-(2-aminothiazol-4-yl)acetyl;
R$^2$ is carboxy; and
Y is hydrogen.

5. The compound of claim 4, which is 7-62 -[2-methoxyimino-2-(2-aminothiazol-4-yl)acetamido]-1-oxadethia-3-cephem-4-carboxylic acid (syn isomer) or its hydrochloride.

6. The compound of claim 4, which is 7β-[2-ethoxyimino-2-(2-aminothiazol-4-yl)acetamido]oxadethia-3-cephem-4-carboxylic acid (syn isomer).

7. The compound of claim 4, which is 7β-[2-isopropoxyimino-2-(2-aminothiazol-4-yl)acetamido]-1-oxadethia-3-cephem-4-carboxylic acid (syn isomer) or its hydrochloride.

8. The compound of claim 4, which is 7β-[2-butoxyimino-2-(2-aminothiazol-4-yl)acetamido]-1-oxadethia-3-cephem-4-carboxylic acid (syn isomer).

9. The compound of claim 4, which is 7β-[2-pentyloxyimino-2-(2-pentyloxyimino-2-(2-amiothiazol-4-yl)acetamido]-1-oxadethia-3-cephem-4-carboxylic acid (syn isomer) or its hydrochloride.

10. The compound of claim 3, wherein
$R^{1a}$ is 2-lower alkoxyimino-2-(2-aminothiazol-4-yl)acetyl;
$R^2$ is carboxy; and
Y is methoxy.

11. The compound of claim 10, which is 7α-methoxy-7β-[2-methoxyimino-2-(2-aminothiazol-4-yl)acetamido]-1-oxadethia-3-cephem-4-carboxylic acid (syn isomer) or its hydrochloride.

12. The compound of claim 3, wherein
$R^{1a}$ is 2-lower alkenyloxyimino-2-(2-aminothiazol-4-yl)acetyl;
$R^2$ is carboxy; and
Y is hydrogen.

13. The compound of claim 12, which is 7β-[2-allyloxyimino-2-(2-aminothiazol-4-yl)acetamido]-1-oxadethia-3-cephem-4-carboxylic acid (syn isomer).

14. The compound of claim 3, wherein
$R^{1a}$ is 2-lower alkynyloxyimino-2-(2-aminothiazol-4-yl)acetyl;
$R^2$ is carboxy; and
Y is hydrogen.

15. The compound of claim 14, which is 7β-[2-(2-propynyloxyimino)-2-(2-aminothiazol-4-yl)acetamido]-1-oxadethia-3-cephem-4-carboxylic acid (syn isomer) or its hydrochloride.

16. The compound of claim 3, wherein
$R^{1a}$ is 2-phenyl(lower)alkoxyimino-2-(2-aminothiazol-4-yl)acetyl;
$R^2$ is carboxy; and
Y is hydrogen.

17. The compound of claim 16, which is 7β-[2-benzyloxyimino-2-(2-aminothiazol-4-yl)acetamido]-1-oxadethia-3-cephem-4-carboxylic acid (syn isomer).

18. The compound of claim 3, wherein
$R^{1a}$ is 2-lower alkoxyimino-2-(5-amino-1,2,4-thiadiazol-3-yl)acetyl;
$R^2$ is carboxy; and
Y is hydrogen.

19. The compound of claim 18, which is 7β-[2-methoxyimino-2-(5-amino-1,2,4-thiadiazol-3-yl)acetamido]-1-oxadethia-3-cephem-4-carboxylic acid (syn isomer).

20. The compound of claim 3, wherein
$R^{1a}$ is 2-lower alkoxyimino-2-(6-aminopyridin-2-yl)acetyl;
$R^2$ is carboxy; and
Y is hydrogen 21. The compound of claim 20, which is 7β-[2-methoxyimino-2-(6-aminopyridin-2-yl)acetamio]-1-oxadethia-3-cephem-4-carboxylic acid (syn isomer) or its hydrochloride.

22. The compound of claim 1, wherein
$R^{1a}$ is 2-lower alkoxyimino-2-(4-aminopyrimidin-2-yl)acetyl;
$R^2$ is carboxy; and
Y is hydrogen.

23. The compound of claim 22, which is 7β-[2-methoxyimino-2-(4-aminopyrimidin-2-yl)acetamido]-1-oxadethia-3-cephem-4-carboxylic acid (syn isomer).

* * * * *